US006455589B1

(12) United States Patent
Ames et al.

(10) Patent No.: US 6,455,589 B1
(45) Date of Patent: Sep. 24, 2002

(54) PRIMARY N-HYDROXYLAMINES

(75) Inventors: Bruce N. Ames, Berkeley, CA (US); Hani Atamna, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/429,412

(22) Filed: Oct. 28, 1999

(51) Int. Cl.$^7$ ................................................ A61K 31/13
(52) U.S. Cl. ...................................................... 514/645
(58) Field of Search ......................................... 514/645

(56) References Cited

U.S. PATENT DOCUMENTS

| 3,644,278 A | | 2/1972 | Klemchuk | 260/482 |
| 3,778,464 A | * | 12/1973 | Klemchuck | 260/482 |
| 3,892,859 A | * | 7/1975 | Linder | 424/250 |
| 3,997,594 A | * | 12/1976 | Alburn et al. | 260/500.5 H |
| 4,673,700 A | | 6/1987 | Ravichandran et al. | 260/481 |
| 5,487,884 A | | 1/1996 | Bissett et al. | 260/482 |
| 5,602,143 A | * | 2/1997 | Krauss | 514/299 |

OTHER PUBLICATIONS

Soukhanov, Editor–in–Chier, of Webster's II, New Riverside University Dictionary, copyright 1988, pp. 358 and 1062.*

* cited by examiner

*Primary Examiner*—Dwayne C. Jones
(74) *Attorney, Agent, or Firm*—Richard Aron Osman

(57) ABSTRACT

The invention provides pharmaceutical compositions comprising primary N-hydroxylamines and related therapeutic, prophylactic, diagnostic and screening methods. The pharmaceutical compositions generally comprise a pharmaceutical composition comprising an orally administrable effective unit solid dosage of a primary N-hydroxylamine or a pharmaceutically acceptable salt thereof and substantially free of a nitrone corresponding to the hydroxylamine.

58 Claims, No Drawings

PRIMARY N-HYDROXYLAMINES

This work was supported by the National Cancer Institute Outstanding Investigator Grant CA39910 and the National Institute of Environmental Health Sciences Center Grant ES01896. The government may have rights in any patent issuing on this application.

FIELD OF THE INVENTION

The field of the invention is pharmaceutical compositions of primary N-hyroxylamines.

BACKGROUND OF THE INVENTION

α-Phenyl-N-t-butyl nitrone (PBN) is one of the most widely used spin trapping agents for investigating the existence of free radicals in biological systems. PBN reverses the age-related oxidative changes in the brains of old gerbils (1,2) and delays senescence in senescence-accelerated mice (3) and in normal mice (4). PBN also delays senescence in the normal human lung fibroblast cell line IMR90 (5). In addition, PBN reverses mitochondrial decay in the liver of old rats (38) and exerts a neuroprotective effect in gerbils (1,7) and rats (8,9) after oxidative damage from ischemia/reperfusion injury. The mechanism underlying the biological activity of PBN is still controversial. However, PBN is a well known scavenger of radical species, though a variety of other well known spin trap or anti-oxidants do not mimic its anti-senescence activity in IMR90. PBN at relatively high concentrations reduces the production of hydrogen peroxide in mitochondrial preparations of cerebral cortex (10) and therefore may exert similar properties in vivo. This suggests that PBN possesses special properties that do not exist in other spin traps or antioxidants.

In the course of our study of the affect of PBN on IMR90 cells we observed that old solutions were more effective than fresh solutions in delaying senescence of IMR90 cells. This raised the question about the interaction of PBN's decomposition products with IMR90 cells. This encouraged us to test the anti-senescent effect of the PBN decomposition products, N-t-butyl hydroxylamine and benzaldehyde on IMR90 cells. PBN (or PBN/⁻OH) has been reported to decompose to N-t-butyl hydroxylamine or N-t-butyl hydronitroxide and benzaldehyde (11–13). PBN, as purchased, often contains N-t-butyl hydroxylamine (14). Benzaldehyde, is both mutagenic (15) and carcinogenic (16). N-t-butyl hydroxylamine is a primary hydroxylamine that can be oxidized, under certain conditions (such as with UV or $Fe^{+3}$), to N-(t-butyl)aminoxyl (also referred as N-t-butyl hydronitroxide (10–12). N-(t-butyl)aminoxyl and the corresponding N-hydroxylamine are primary amines and are thus different from the well known cyclic-nitroxides/cyclic-hydroxylamines. The antioxidative and protective features of some cyclic-nitroxides/cyclic-hydroxylamines are known. Probably the most important feature in this regard, is their ability to catalyze superoxide radical dismutation to form $H_2O_2$ (17–21). In vitro cyclic-nitroxides can either be oxidized to oxo-ammonium cation or reduced to the corresponding hydroxylamine by superoxide radical, depending on the type of cyclic-nitroxide. Thus cyclic-hydroxylamine or the corresponding oxo-ammonium cation are intermediates during the dismutation of superoxide radical by nitroxide. Interestingly, the oxo-ammonium cation species is reduced to the corresponding cyclic-hydroxylamine by the cellular reductant NADH, which suggests that cyclic-hydroxylamine can be the dominant form inside the cells. In addition the cyclic-nitroxide species can undergo one electron reduction to the corresponding cyclic-hydroxylamine, a reaction proposed to be mediated by mitochondrial coenzyme Q and ascorbic acid (21–23). Mitochondrial cytochrome c oxidase can also oxidize the cyclic-hydroxylamine to the corresponding nitroxide (24). Thus, it appears that mitochondria can contribute to the cycling of cyclic-nitroxides/cyclic-hydroxylamines, which in turn can facilitate dismutation of superoxide radical to $H_2O_2$. The N-t-butyl hydroxylamine and the other N-hydroxylamines tested in this study are primary N-hydroxylamines which have not been previously examined as antioxidants.

SUMMARY OF THE INVENTION

The invention provides pharmaceutical compositions comprising primary N-hydroxylamines and related therapeutic, prophylactic, diagnostic and screening methods.

The pharmaceutical compositions generally comprise a pharmaceutical composition comprising an orally administrable effective unit solid dosage of a primary N-hydroxylamine or a pharmaceutically acceptable salt thereof and substantially free of a nitrone corresponding to the hydroxylamine, wherein the hydroxylamine has the formula:

$R_iNHOH$ wherein $R_i$ is independently selected from: substituted or unsubstituted (C1–C18) alkyl, alkenyl, alkynyl, aryl (carbocyclic and heterocyclic), oxyl, acyl, carboxyl, amino, nitro, nitroso, oxime, hydrazone, azo, thiol, sulfonyl and halide.

In a first particular embodiment of the general compositions, $R_i$ is substituted or unsubstituted methyl group having the general formula,

$NHOHCR_1R_2R_3$ wherein $R_1$, $R_2$ and $R_3$ are independently selected from: substituted or unsubstituted (C0–C10) alkyl, alkenyl, alkynyl, aryl (carbocyclic and heterocyclic), oxyl, acyl, carboxyl, amino, nitro, nitroso, oxime, hydrazone, azo, thiol, sulfonyl and halide.

The invention provides more specific aspects of this embodiment:

wherein at least one R of $R_1$, $R_2$ and $R_3$ is selected from unsubstituted (C0–C10) alkyl, alkenyl and alkynyl;

wherein at least one R of $R_1$, $R_2$ and $R_3$ is selected from unsubstituted (C0–C18) alkyl, cycloalkyl, alkenyl and alkynyl, and the R is selected from: $CH_3$—$(CH_2)_{n1}$, $(CH_3$—$(CH_2),2$—$)_2$ CH, $(CH_3$—$(CH_2)_2$—$)_3$, cyclopentyl, cyclohexyl, $(CH_2$=$CH$—$CH_2)_{n3}$ and $(CH$=$C$—$CH_2$—$)_{n3}$, wherein n1=1 to 18, n2=1 to 17 and n3=1 to 3;

wherein at least one R of $R_1$, $R_2$ and $R_3$ is selected from unsubstituted (C0–C10) alkyl, alkenyl and alkynyl, and the hydroxylamine is selected from:

| | |
|---|---|
| N-methylhydroxylamine, | N-(n-decahexyl)hydroxylamine, |
| N-ethylhydroxylamine, | N-(n-decaoctyl)hydroxylamine, |
| N-n-propylhydroxylamine, | N-isopropylhydroxylamine, |
| N-(n-butyl) hydroxylamine, | N-sec-butylhydroxylamine, |
| N-(n-pentyl)hydroxylamine, | N-tert-butylhydroxylamine, |
| N-(n-hexyl)hydroxlamine, | N-cyclohexylhydroxylamine, |
| N-(n-heptyl)hydroxylamine, | N-cyclopentylhydroxylamine, |
| N-(n-octyl)hydroxylamine, | N-(2-propene)hydroxylamine, |

-continued

| | |
|---|---|
| N-(n-nonyl)hydroxylamine, | N-(3-butene)hydroxylamine, |
| N-(n-decyl)hydroxylamine, | N-(2-propyne)hydroxylamine and |
| N-(n-dodecyl)hydroxylamine, | N-(3-butyne)hydroxylamine; | wherein at least one R of $R_1$, $R_2$ and $R_3$ is substituted or unsubstituted aryl;

wherein at least one R of $R_1$, $R_2$ and $R_3$ is substituted or unsubstituted aryl, and the R is selected from: mono, di, or tri methyl, methoxy, halo, nitro, amino, hydroxyl and substituted or unsubstituted phenyl, naphthyl, anthryl, phenanthryl, pyridyl, quinolinyl, imidazolyl, benzoxazolyl, pyrrolyl, furanyl, piperidinolyl and tetrahydrofuranyl;

wherein at least one R of $R_1$, $R_2$ and $R_3$ is substituted or unsubstituted aryl, and the hydroxylamine is selected from:

| | |
|---|---|
| N-benzylhydroxylamine, | N-(1,3-diaminobenzyl)hydroxylamine, |
| N-(n-nitrobenzyl)hydroxylamine, | N-(1,3-hydroxybenzyl)hydroxylamine, |
| N-(n-methylbenzyl)hydroxylamine, | N-(2,4-diaminobenzyl)hydroxylamine, |
| N-(n-chlorobenzyl)hydroxylamine, | N-(2,4-dihydroxybenzyl)hydroxylamine, |
| N-(n-aminobenzyl)hydroxylamine, | Imidazole-2-methylhydroxylamine and |
| N-(n-hydroxybenzyl)hydroxylamine, | Benzoxazole-2-methylhydroxylamine, | wherein n is selected from 1, 2, 3, 4, 5 and 6;

wherein at least one R of $R_1$, $R_2$ and $R_3$ is substituted or unsubstituted (C0–C18) oxyl;

wherein at least one R of $R_1$, $R_2$ and $R_3$ is substituted or unsubstituted (C0–C18) oxyl and the R is selected from: hydroxyl, hydroxyalkyl (HO—$(CH_2)_{n1}$), hydroxyaryl selected from benzylalcohol, phenol and naphthol, alkoxy (O—$(CH_2)_{n1}$) and aryloxy selected from phenoxy, benzyloxy and naphthyloxy, wherein n1=1 to 18;

wherein at least one R of $R_1$, $R_2$ and $R_3$ is substituted or unsubstituted (C0–C18)alkyl hydroxyl or arylhydroxyl and the hydroxylamine is selected from:

| | |
|---|---|
| N-(hydroxymethyl)hydroxylamine, | N-(methoxymethyl)hydroxylamine, |
| N-(2-hydroxyethyl)hydroxylamine, | N-(methoxyethyl)hydroxylamine, |
| N-(3-hydroxypropyl)hydroxylamine, | N-(methoxyisopropyl)hydroxylamine, |
| N-(4-hydroxybutyl)hydroxylamine, | N-(benzyloxymethyl)hydroxylamine and |
| N-(6-hydroxyhexyl)hydroxylamine, | N-(4-hydroxymethylbenzyl)hydroxylamine; |
| N-(12-hydroxydodecyl)hdyroxylamine, | | wherein at least one R of $R_1$, $R_2$ and $R_3$ is substituted or unsubstituted (C0–C18) alkylcarboxyl or arylcarboxyl;

wherein at least one R of $R_1$, $R_2$ and $R_3$ is substituted or unsubstituted (C0–C18) alkyl or aryl carboxyl and the R is selected from carboxyalkyls and benzyl;

wherein at least one R of $R_1$, $R_2$ and $R_3$ is substituted or unsubstituted alkyl (C0–C18) or arylcarboxyl and the hydroxylamine is selected from:

| | |
|---|---|
| N-(carboxymethyl)hydroxylamine, | N-(5-carboxypentyl) hydroxylamine, |
| N-(2-carboxyethyl)hydroxylamine, | N-(6-carboxyhexyl)hydroxylamine, |
| N-(3-carboxypropyl)hydroxylamine, | N-(4-carboxybenzyl)hydroxylamine and |
| N-(4-carboxybutyl)hydroxylamine, | N-(12-carboxydodecyl)hydroxylamine; | wherein at least one R of $R_1$, $R_2$ and $R_3$ is substituted or unsubstituted (C0–C18) ester;

wherein at least one R of $R_1$, $R_2$ and $R_3$ is substituted or unsubstituted (C0–C18) ester and the R is selected from alkyl (C0–C18) and aryl esters;

wherein at least one R of $R_1$, $R_2$ and $R_3$ is substituted or unsubstituted alkyl (C0–C18) or arylesters and the hydroxylamine is selected from:
N-(acetyloxymethyl)hydroxylamine,
N-(acetyloxyethyl)hydroxylamine,
N-(acetyloxypropyl)hydroxylamine,
N-(propylcarbonyloxy)methylhydroxylamine,
N-(butylcarboxyloxy)methylhydroxylamine,
N-(tert-butyloxycarboxyl)methylhdyroxylamine,
N-(benzyloxycarbonyl)methylhydroxylamine,
N-(phenyloxycarbonyl)methylhydroxylamine,
N-(3-pyridyloxycarbonyl)methylhydroxylamine and
N-(benzoxazol-5-carbonyloxy)methylhydroxylamine;

wherein at least one R of $R_1$, $R_2$ and $R_3$ is substituted or unsubstituted (C0–C18) carbonyl;

wherein at least one R of $R_1$, $R_2$ and $R_3$ is substituted or unsubstituted carbonyl and the R is selected from alkyl (C0–C18) carbonyls and aryl carbonyls;

wherein at least one R of $R_1$, $R_2$ and $R_3$ is substituted or unsubstituted alkyl (C0–C18) or arylcarbonyls and the hydroxylamine is selected from:

| | |
|---|---|
| N-(acetyl)methylhydroxylamine, | N-(phenylcarbonyl)methylhydroxylamine |
| N-(ethylcarbonyl)methylhydroxylamine, | and |
| N-(butylcarbonyl)methylhydroxylamine, | N-(benzylcarbonyl)methylhydroxylamine; | wherein at least one R of $R_1$, $R_2$ and $R_3$ is substituted or unsubstituted alkyl (C0–C18) or aryl amino;

wherein at least one R of $R_1$, $R_2$ and $R_3$ is substituted or unsubstituted alkyl (C0–C18) or aryl amino and the R is selected from primary alkyl amine selected from methylamine, ethylamine, propylamine, butylamine and hexylamine, secondary amine selected from dimethylamine, diethylamine and dipropylamine, tertiary amine selected from trimethyl and trietylamine, and quaternary amine selected from tetramethyl and tetra-ethylammonium salts;

wherein at least one R of $R_1$, $R_2$ and $R_3$ is substituted or unsubstituted alkyl(C0–C18) or aryl amine and the hydroxylamine is selected from:
N-aminomethylhydroxylamine,
N-(2-aminoethyl)hydroxlamine,
N-(N-methylamino)methylhydroxylamine,
N-(N,N-dimethylamino)methylhydroxylamine,
N-(N,N,N-trimethylammonium) methylhydroxylamine,
N-(3-aminopropyl)hydroxylamine, N-(6-aminohexyl)hydroxylamine,
N-(4-aminobenzyl)hydroxylamine,
Hydroxylamine -1-methylpyridinium and
Hydroxylamine-1-methylquinolinium;

wherein at least one R of $R_1$, $R_2$ and $R_3$ is substituted or unsubstituted (C0–C18) alkyl or aryl nitro;

wherein at least one R of $R_1$, $R_2$ and $R_3$ is substituted or unsubstituted alkyl(C0–C18) or aryl nitro and the R is selected from alkylnitro selected from nitromethyl, nitroethyl, nitropropyl, nitrobutyl, nitropentyl, nitrohexyl and nitrobenzyl, and arylnitro selected from nitrophenyl and nitronaphthyl;

wherein at least one R of $R_1$, $R_2$ and $R_3$ is substituted or unsubstituted alkyl (C0–C18) or aryl nitro and the hydroxylamine is selected from:

| | |
|---|---|
| N-(nitromethyl)hydroxylamine, | N-(5-nitropentyl)hydroxylamine, |
| N-(2-nitroethyl)hydroxylamine, | N-(6-nitrohexyl)hydroxylamine, |
| N-(3-nitropropyl)hydroxylamine, | N-(4-nitrobenzyl)hydroxylamine and |
| N-(4-nitrobutyl)hydroxylamine, | N-(2,4-dinitrobenzyl)hydroxylamine; | wherein at least one R of $R_1$, $R_2$ and $R_3$ is substituted or unsubstituted (C0–C18) nitroso;

wherein at least one R of $R_1$, $R_2$ and $R_3$ is substituted or unsubstituted (C0–C18) nitroso and the R is selected from aliphatic nitrosoamines and aromatic nitroso;

wherein at least one R of $R_1$, $R_2$ and $R_3$ is substituted or unsubstituted nitroso (C0–C18) and the hydroxylamine is selected from:
N-(N-methyl-N-nitroso-amino)methyl hydroxylamine,
N-(N-methyl-N-nitroso-2-amino)ethylhydroxylamine,
N-(N-methyl-N-nitroso-3-amino) propylhydroxylamine and
N-(p-nitroso)benzylhydroxylamine;

wherein at least one R of $R_1$, $R_2$ and $R_3$ is substituted or unsubstituted oxime;

wherein at least one R of $R_1$, $R_2$ and $R_3$ is substituted or unsubstituted (C0–C18) oxime and the R is selected from: acetaldoxime, propionaldoxime, butanaldoxime and benzaldoxime;

wherein at least one R of $R_1$, $R_2$ and $R_3$ is substituted or unsubstituted oxime (C0–C18) and the hydroxylamine is selected from:

| | |
|---|---|
| Acetaldoxime-3-hydroxylamine, | Butanaldoxime-5-hydroxylamine and |
| Propionaldoxime-4-hydroxylamine, | (4-benzaldoxime)1-methylhydroxylamine; | wherein at least one R of $R_1$, $R_2$ and $R_3$ is substituted or unsubstituted (C0–C10) hydrazone; p1 wherein at least one R of $R_1$, $R_2$ and $R_3$ is substituted or unsubstituted (C0–C10) hydrazone and the R is selected from: acetaldehyde hydrazone, propanaldehyde hydrozone, butanaldehyde hydrazone and phenylhydrazone;

wherein at least one R of $R_1$, $R_2$ and $R_3$ is substituted or unsubstituted hydrazone (C0–C10) and the hydroxylamine is selected from:

| | |
|---|---|
| 1-hydroxylamine-acetaldehyde hydrazone, | 1-hydroxylamine-butanal-dehyde hydrazone and |
| 1-hydroxylamine-propanaldehyde hydrazone, | 1-hydroxylamine-benzyl-aldehyde hydrazone; | wherein at least one R of $R_1$, $R_2$ and $R_3$ is substituted or unsubstituted azo;

wherein at least one R of $R_1$, $R_2$ and $R_3$ is substituted or unsubstituted azo and the R is selected from: azobenzene, p-(phenylazo)benzyl and p-diazobenzyl;

wherein at least one R of $R_1$, $R_2$ and $R_3$ is substituted or unsubstituted azo and the hydroxylamine is selected from:
N-(p-phenylazo)benzylhydroxylamine,
N-(p-diazobenzyl)hydroxylamine and
N-(p-methoxyphenylazo)benzylhydroxylamine wherein at least one R of $R_1$, $R_2$ and $R_3$ is substituted or unsubstituted (C0–C18) thiol;

wherein at least one R of $R_1$, $R_2$ and $R_3$ is substituted or unsubstituted (C0–C18) thiol and the R is selected from (C0–C18) alkylthiol selected from methyl, ethyl, propyl, butyl, pentyl and hexyl thiol, and arylthiol selected from thiophenol and benzylthiol;

wherein at least one R of $R_1$, $R_2$ and $R_3$ is substituted or unsubstituted (C0–C18) thiol and the hydroxylamine is selected from:

| | |
|---|---|
| N-(thiomethyl)hydroxylamine, | N-(3-thiopropyl)hydroxylamine and |
| N-(2-thioethyl)hydroxylamine, | N-(p-sulfhydryl)benzylhydroxylamine; | wherein at least one R of $R_1$, $R_2$ and $R_3$ is substituted or unsubstituted (C0–C18) sulfonic acid;

wherein at least one R of $R_1$, $R_2$ and $R_3$ is substituted or unsubstituted (C0–C18) sulfonic acid and the R is selected from methanesulfonic acid, ethanesulfonic acid, propanesulfonic acid, butanesulfonic acid and p-toluenesulfonic acid;

wherein at least one R of $R_1$, $R_2$ and $R_3$ is substituted or unsubstituted (C0–C18) sulfonic acid and the hydroxylamine is selected from:

| | |
|---|---|
| 1-hydroxylamine-methanesulfonic acid, | 1-hydroxylamine-butane-4-sulfonic acid |
| 1-hydroxylamine-ethane-2-sulfonic acid, | and |
| 1-hydroxylamine-propane-3-sulfonic acid, | N-(p-sulfobenzyl)hydroxylamine; | wherein at least one R of $R_1$, $R_2$ and $R_3$ is halide;

wherein at least one R of $R_1$, $R_2$ and $R_3$ is halide and the R is selected from F, Cl, Br and wherein at least one R of $R_1$, $R_2$ and $R_3$ is halide and the hydroxylamine is selected from:

| | |
|---|---|
| N-(chloromethyl)hydroxylamine, | N-(4-chlorobutyl)hydroxylamine, |
| N-(bromomethyl)hydroxylamine, | N-(p-chlorobenzyl)hydroxylamine, |
| N-(2-chloroethyl)hydroxylamine, | N-(p-fluorobenzyl)hydroxylamine and |
| N-(3-chloropropyl)hydroxylamine, | N-(p-iodobenzyl)hydroxylamine; | wherein at least one R of $R_1$, $R_2$ and $R_3$ is substituted or unsubstituted hydroxylamine;

wherein at least one R of $R_1$, $R_2$ and $R_3$ is substituted or unsubstituted hydroxylamine and R is selected from N-methylhydroxylamine, N-ethylhydroxylamine, N-propylhydroxylamine N-butylhydroxylamine, N-pentylhydroxylamine, and N-benzylhydroxylamine;

wherein at least one R of $R_1$, $R_2$ and $R_3$ is is substituted or unsubstituted hydroxylamine and the hydroxylamine is selected from:

| | |
|---|---|
| Bis-methylhydroxylamine, | Bis-(3-propyl)hydroxylamine and |
| Bis-(2-ethyl)hydroxylamine, | Bis-benzylhdyroxylamine; | wherein at least one R of $R_1$, $R_2$ and $R_3$ is substituted or unsubstituted (C0–C18) phosphoester;

wherein at least one R of $R_1$, $R_2$ and $R_3$ is substituted or unsubstituted (C0–C18) phosphoester and the R is selected from: dimethylphosphate, diethylphosphate, dipropylphosphate and benzylphosphate;

wherein at least one R of $R_1$, $R_2$ and $R_3$ is substituted or unsubstituted (C0–C18) phosphoester and the hydroxylamine is selected from:
di-hydroxylaminemethylphosphate ester,
mono-hydroxylaminemethylphosphate ester,
mono-(1-hydroxylamine)-ethyl-2-phosphate ester,
di-(1-hydroxylamine)-2-ethylphosphate ester,
di-(1-hydroxylamine)-3-propyl-phosphate ester,
mono-(hydroxylamine-benzyl-phosphate ester and
di-hydroxylamine-benzylphosphateester.

In a second particular embodiment of the general compositions, $R_i$ is substituted or unsubstituted carbonyl. The invention provides more specific aspects of this embodiment:

wherein $R_i$ is substituted or unsubstituted carbonyl group and R is selected from: methyl, ethyl, propyl, butyl and pentyl, hexyl ketones, and aromatic ketone selected from phenyl, naphthyl and anthryl ketone; and wherein $R_i$ is substituted or unsubstituted carbonyl group and R is selected from alkyl (C0–C18) or aryl carbonyl and the hydroxylamine is selected from:

| | |
|---|---|
| Hydroxyurea ($NH_2CONHOH$), | N-(tert-butoxycarbonyl)-hydroxylamine, |
| N-(acetyl)hydroxylamine, | N-(carbonylphenyl)hydroxylamine and |
| N-(carbonylethyl)hydroxylamine, | N-(benzylcarbonyl)hydroxylamine. |
| N-(carbonylpropyl)hydroxylamine, | |

In a third particular embodiment of the general compositions, $R_i$ is substituted or unsubstituted carboxylic acid. The invention provides more specific aspects of this embodiment:

wherein $R_i$ is substituted or unsubstituted carboxylic acid and R is selected from aliphatic acids selected from methyl, ethyl, propyl, butyl, pentyl and hexanoic acids, and aromatic acids selected from benzoic acid; and wherein $R_i$ is substituted or unsubstituted carboxylic acid and R is selected from alkyl (C0–C18) or aryl acid the hydroxylamine is selected from:

| | |
|---|---|
| N-(acetyoxy)hydroxylamine, | N-(butylcarbonyloxy)-hydroxylamine, |
| N-(ethylcarbonyloxy)hydroxylamine, | N-(phenylcarbonyloxy)-hydroxylamine and |
| N-(propylcarbonyloxy)hydroxylamine, | N-(benzylcarbonyloxy)-hydroxylamine. |

Other particular embodiments include:
wherein the dosage is from 100 ug to 1 g;
wherein the nitrone is less than 10%, 1%, 0.1% (wt/wt) of the hydroxylamine in the composition;
wherein the composition is packaged with a label identifying the primary N-hydroxylamine and prescribing a pharmaceutical use thereof, particularly wherein the use is other than oncological and/or comprises reducing oxidative damage or delaying senescence; and
wherein the composition further comprising an effective amount of a carnitine.

The invention also provides a wide variety of methods of using primary N-hydroxylamines, including the subject hydroxylamines, including:

a method for reducing oxidative damage to, or delaying senescence of a cell comprising the steps of: identifying a cell as subject to or at risk of undesirable oxidative damage or senescence; and contacting the cell with a composition comprising an effective amount of a primary hydroxylamine and substantially free of a nitrone corresponding to the hydroxylamine, particularly, wherein the cell is contained in other than a cancerous host;

a method for screening for primary N-hydroxylamines which reduce oxidative damage to, or delay senescence of cells, comprising the steps of: contacting cells with a candidate primary N-hydroxylamine under conditions whereby, but for the presence of the hydroxylamine, the cells present a reference amount of oxidative damage or senescence; detecting post-treatment amounts of oxidative damage or senescence of the cells; wherein a lesser amount of post-treatment than reference amounts of oxidative damage or senescences indicates that the hydroxylamine reduces oxidative damage or delays senescence of the cells;

a method for improving short term memory in a patient, said method comprising administering to said patient a pharmaceutical composition comprising an effective short term memory improving amount of a subject hydroxylamine;

a method for treating a patient with an acute central nervous system disorder, said method comprising administering to said patient a pharmaceutical composition comprising an effective acute central nervous system disorder-treating amount of a subject hydroxylamine, particularly wherein the acute central nervous system disorder treated is stroke;

a method for treating a patient with an acute cardiovascular disorder, said method comprising administering to said patient a pharmaceutical composition comprising an effective acute cardiovascular disorder-treating amount of a subject hydroxylamine, particularly wherein the acute cardiovascular disorder treated is cardiac infarction;

a method for treating a patient with a neurodegenerative disease which method comprises administering to said patient a pharmaceutical composition comprising an effective neurodegenerative disease-treating amount of a subject hydroxylamine, and a method for preventing the onset of a neurodegenerative disease in a patient at risk for developing the neurodegenerative disease which method comprises administering to said patient a pharmaceutical composition comprising an effective neurodegenerative disease-preventing amount of a subject hydroxylamine, particularly wherein the neurodegenerative disease treated and/or prevented in the above methods is Alzheimer's disease, Parkinson's disease, HIV dementia and the like;

a method for treating a patient with an autoimmune disease which method comprises administering to said patient a pharmaceutical composition comprising an effective autoimmune disease-treating amount of a subject hydroxylamine, and a method for preventing the onset of an autoimmune disease in a patient at risk for developing the autoimmune disease which method comprises administering to said patient a pharmaceutical composition comprising an effective autoimmune disease-preventing amount of a subject hydroxylamine, particularly wherein the autoimmune disease treated and/or prevented in the above methods is systemic lupus, multiple sclerosis and the like;

a method for treating a patient with an inflammatory disease which method comprises administering to said patient a pharmaceutical composition comprising an effective inflammatory disease-treating amount of a subject hydroxylamine, and a method for preventing the onset of an inflammatory disease in a patient at risk for developing the inflammatory disease which method comprises administering to said patient a pharmaceutical composition comprising an effective inflammatory disease-preventing amount of a subject hydroxylamine, particularly wherein the inflammatory disease treated and/or prevented in the above methods is rheumatoid arthritis, septic shock, erythema nodosum leprosy, septicemia, uveitis and the like.

DETAILED DESCRIPTION OF SPECIFIC EMBODIMENTS OF THE INVENTION

The following descriptions of particular embodiments and examples are offered by way of illustration and not by way of limitation.

Definitions

Unless contraindicated or noted otherwise, in these descriptions and throughout this specification, the terms "a" and "an" mean one or more, the term "or" means and/or.

"Alkyl" refers to monovalent alkyl groups preferably having from 1 to about 18 carbon atoms, more preferably 1 to 8 carbon atoms and still more preferably 1 to 6 carbon atoms. This term is exemplified by groups such as methyl, ethyl, n-propyl, isopropyl, n-butyl, sec-butyl, tert-butyl, n-hexyl, n-octyl, tert-octyl and the like. The term "lower alkyl" refers to alkyl groups having 1 to 6 carbon atoms.

"Substituted alkyl" refers to an alkyl group preferably having from 1 to about 12 carbon atoms, more preferably 1 to 8 carbon atoms and still more preferably 1 to 6 carbon atoms, which is substituted, preferably with, from 1 to 3 substituents selected from the group consisting of alkoxy, amino, mono- and dialkylamino, aminoacyl, amido, alkoxycarbonyl, aryl, carboxyl, cyano, halo, heterocyclic, hydroxy, nitro, thioalkoxy and the like.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH2), n-propenyl (—CH2 CH=CH2), isopropenyl (—C(CH3)=CH2), and the like.

"Alkynyl" refers to alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—CH2C≡CH), and the like.

"Alkcycloalkyl" refers to -alkylene-cycloalkyl groups preferably having from 1 to 10 carbon atoms in the alkylene moiety and from 3 to 8 carbon atoms in the cycloalkyl moiety.

Such alkcycloalkyl groups are exemplified by —CH2-cyclopropyl, —CH2-cyclopentyl, —CH2CH2-cyclohexyl, and the like.

"Alkoxy" refers to the group "alkyl-O—". Preferred alkoxy groups include, by way of example, methoxy, ethoxy, n-propoxy, isopropoxy, n-butoxy, tert-butoxy, sec-butoxy, n-pentoxy, n-hexoxy, 1,2-diethylbutoxy, and the like.

"Alkoxycarbonyl" refers to the group —C(O)OR where R is alkyl. "Aminocarbonyl" refers to the group —C(O)NRR where each R is independently hydrogen or alkyl.

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted, preferably with from 1 to 3 substituents selected from the group consisting of alkyl, substituted alkyl, alkoxy, alkenyl, alkynyl, amino, aminoacyl, aminocarbonyl, alkoxycarbonyl, aryl, carboxyl, cyano, halo, hydroxy, nitro, trihalomethyl and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Halo" or "halogen" refers to fluoro, chloro, bromo and iodo. Preferred halo groups are either fluoro or chloro.

"Thioalkoxy" refers to the group "alkyl-S—". Preferred thioalkoxy groups include, by way of example, thiomethoxy, thioethoxy, n-thiopropoxy, isothiopropoxy, n-thiobutoxy and the like.

"Heterocycle" or "heterocyclic" refers to a monovalent saturated or unsaturated group having a single ring or multiple condensed rings, from 1 to 10 carbon atoms and from 1 to 4 hetero atoms selected from nitrogen, sulfur or oxygen within the ring. Examples of heterocycles include, but are not limited to, morpholine, piperazine, imidazolidine, pyrrolidine, piperidine and the like.

"Pharmaceutically acceptable salt" refers to pharmaceutically acceptable salts which are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate and the like. Pharmaceutically acceptable salts of the hydroxylamines of this invention are prepared using conventional procedures well known to those skilled in the art including, for example, treating a sulfonic acid derivative with an appropriate base.

A corresponding nitrone means a nitrone condensate of the hydroxylamine and hence, having the same nitrogen bound R group, i.e. the condensation product of the primary N-hyroxyl amine with an aldehyde. Substantially free of a corresponding nitrone means the nitrone is less than 10%, preferably less than 1%, more preferably less than 0.1% (wt/wt) of the corresponding hydroxylamine in the composition.

Orally administrable means both safe and effective when orally administered.

General Synthetic Procedures

The hydroxylamine compounds of this invention can be purchased commercially and/or prepared from readily available starting materials using conventional methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The hydroxylamine may often be prepared by reduction of the corresponding nitro compound using a suitable catalyst such as an activated zinc/acetic acid catalyst or an aluminum/mercury amalgam catalyst. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc catalyst or an ether/water mixture in the case of the aluminum amalgam catalyst. Hydroxylamines can also be prepared by reduction of oximes with hydride reducing agents, such as sodium cyanoborohydride. Aliphatic nitro compounds (in the form of their salts) can also be reduced to hydroxylamines. Since some hydroxylamines have limited stability, such compounds are generally prepared immediately prior to reaction with a carbonyl compound. Alternatively, hydroxylamines can often be stored (or purchased commercially) as their hydrochloride salts. In such cases, the free hydroxylamine is typically generated immediately prior to reaction with a carbonyl compound by reaction of the hydrochloride salt with a suitable base, such as sodium hydroxide, sodium methoxide and the like.

In a particular embodiment, at least one of $R_1$, $R_2$ and $R_3$ is selected from the group consisting of alkyl, substituted alkyl, alkenyl, alkynyl, alkaryl, aryl, alkcycloalkyl, cycloalkyl and cycloalkenyl; particularly wherein $R_1$ is selected from the group consisting of alkyl, substituted alkyl, alkenyl, alkynyl, alkaryl, aryl, alkcycloalkyl, cycloalkyl and cycloalkenyl and $R_2$ and $R_3$ are H. Preferred hydroxylamines of this invention include, but are not limited to, N-methylhydroxylamine, N-ethylhydroxylamine, N-n-propylhydroxylamine, N-isopropylhydroxylamine, N-n-butylhydroxylamine, N-isobutylhydroxylamine, N-sec-butylhydroxylamine, N-tert-butylhydroxylamine, N-n-pentylhydroxylamine, N-cyclopentylhydroxylamine, N-n-hexylhydroxylamine, N-cyclohexylhydroxylamine, N-n-octylhydroxylamine, N-tert-octylhydroxylamine, N-phenylhydroxylamine and the like. Also included are compounds having multiple primary hydroxylamine moieties, e.g. methyl di(hydroxylamine).

In some cases, the hydroxylamines of this invention will contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the disclosed hydroxylamines are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Pharmaceutical Compositions

When employed as pharmaceuticals, the hydroxylamines of this invention are typically administered in the form of a pharmaceutical composition comprising at least one active hydroxylamine compound and a carrier, vehicle or excipient suitable for use in pharmaceutical compositions. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition. Such carriers are well known in the pharmaceutical art as are procedures for preparing pharmaceutical compositions.

Depending on the intended route of delivery, the compositions may be administered in one or more dosage form(s) including, without limitation, liquid, solution, suspension, emulsion, tablet, multi-layer tablet, bi-layer tablet, capsule, gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, or infusion.

The dosage forms may include a variety of other ingredients, including binders, solvents, bulking agents, plasticizers etc. Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide. The plasticizers used in the dissolution modifying system are preferably previously dissolved in an organic solvent and added in solution form. Preferred plasticizers may be selected from the group consisting of diethyl phthalate, diethyl sebacate, triethyl citrate, crotonic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble drugs, such as potassium chloride. In contrast, hydrophilic plasticizers are used when water-insoluble drugs are employed which aid in dissolving the encapsulating film, making channels in the surface, which aid in drug release.

A wide variety of orally administerable compositions may be used. In a particular embodiment, the oral compositions are provided in solid discrete, self-contained dosage units, such as tablets, caplets, lozenges, capsules, gums, etc., which may comprise or be filled with liquid or solid dosage of the hydroxylamine. A wide variety of dosages may be used, depending on the application and empirical determination; typical dosages range from 10 ug to 1 g, preferably at least 100 ug, more preferably at least 1 mg, more preferably at least 10 mg, most preferably at least 100 mg.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the hydroxylamine compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the hydroxylamine compound in such compositions is typically a minor component, often being from about 0.05 to 10% by weight with the remainder being the injectable carrier and the like.

The above described components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The dosage forms of the present invention involve the administration of an active therapeutic substance or multiple active therapeutic substances in a single dose during a 24 hour period of time or multiple doses during a 24 hour period of time. The doses may be uneven in that each dose is different from at least one other dose.

The subject compositions may be administered to effect various forms of release, which include, without limitation, immediate release, extended release, controlled release, timed release, sustained release, delayed release, long acting, pulsatile delivery, etc., using well known procedures and techniques available to the ordinary skilled artisan. A description of representative sustained release materials can be found in the incorporated materials in Remington's Pharmaceutical Sciences.

The following formulation examples illustrate representative pharmaceutical compositions of this invention. The present invention, however, is not limited to the following exemplified pharmaceutical compositions.

Formulation 1—Tablets: A compound (e.g. tert-buytlhydroxylamine) is admixed as a dry powder with a dry gelatin binder in an approximate 1:2 weight ratio. A minor amount of magnesium stearate is added as a lubricant. The mixture is formed into 240–270 mg tablets (80–90 mg of active hydroxylamine compound per tablet) in a tablet press.

Formulation 2—Capsules: A compound (e.g. tert-buytlhydroxylamine) is admixed as a dry powder with a starch diluent in an approximate 1:1 weight ratio. The mixture is filled into 250 mg capsules (125 mg of active hydroxylamine compound per capsule).

Formulation 3—Liquid: A compound (e.g. tert-buytlhydroxylamine) (50 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets: The compound (e.g. tert-buytlhydroxylamine) is admixed as a dry powder with a dry gelatin binder in an approximate 1:2 weight ratio. A minor amount of magnesium stearate is added as a lubricant. The mixture is formed into 450–900 mg tablets (150–300 mg of active hydroxylamine compound) in a tablet press.

Formulation 5—Injection: The compound (e.g. tert-buytlhydroxylamine) is dissolved in a buffered sterile saline injectable aqueous medium to a concentration of approximately 5 mg/ml.

Formulation 6-Ointment: The compound (e.g. tert-buytlhydroxylamine) (2 g) is blended with isopropyl myristate 81 g, fluid paraffin oil 9 g and silica (Aerosil 200, 9 g, Degussa AG, Frankfurt).

Formulation 7-Ointment: The compound (e.g. tert-buytlhydroxylamine) (23 g) is blended with pharmaceutical-grade white 100 g petroleum jelly.

Formulation 8-Non-ionic water-in-oil cream: The compound (e.g. tert-buytlhydroxylamine) (100 g) is blended with a mixture of emulsified lanolin 39 g alcohols, of waxes and of oils (Anhydrous eucerin, BDF), methyl para-hydroxybenzoate 0.075 g, propyl para-hydroxybenzoate 0.075 g and sterile demineralized 100 g water.

Formulation 9—Lotion: The compound (e.g. tert-buytlhydroxylamine) (2 g) is blended with polyethylene glycol (PEG 400) 69 g and 95% Ethanol 30 g.

Formulation 10—Hydrophobic ointment: The compound (e.g. tert-buytlhydroxylamine) (2 g) is blended with isopropyl myristate 36 g, silicone oil (Rhodorsil 36.400 g 47 V 300, Rhone-Poulenc), beeswax 13 g and silicone oil (Abil 300 100 g cst, Goldschmidt).

Formulation 11—Non-ionic oil-in-water cream: The compound (e.g. tert-buytlhydroxylamine) (2 g) is blended with cetyl alcohol 4 g, glyceryl monostearate 2.5 g, PEG 50 stearate 2.5 g, Karite butter 9.2 g, propylene glycol 2.0 g, methyl para-hydroxybenzoate 0.075 g, propyl para-hydroxybenzoate 0.075 g and sterile demineralized 100 g water.

Applications

As therapeutics and/or prophylactics, the hydroxylamines of this invention have been found to be useful for treating a wide variety of medical dysfunctions and diseases, in humans and animal. Among the various medical conditions which may be prevented and/or treated, the hydroxylamines of this invention are particularly useful for treating conditions involving acute oxidate damage, such as acute intense oxidative damage to a region of the central nervous system, e.g. stroke, conditions associated with stroke, concussion and subarachnoid hemorrhage or chronic oxidate damage, such as is associated with senescene and aging. Accordingly, the subject compositions are useful in treating a variety of dysfunctions or disorders characterized by oxidized proteins, nucleic acids or lipids in the tissues, cells, or associated fluids (such as the blood). Cellular, tissue, systemic and organismal indicia of oxidative damage are known in the art and exemplified below; for example, in vitro cellular oxidative damage and senscence may be measured as described in Chen et al. (1995) Proc.Natl.Acad.Sci.USA 92, 4337–4341.

Disorders are generally divided into disorders of the central and peripheral nervous system and disorders of the peripheral organs. Disorders of the CNS include stroke, aging, neurodegenerative conditions, such as Alzheimer's disease, Parkinsonism, concussion, aneurysm, ventricular hemorrhage and associated vasospasm, migraine and other vascular headaches, spinal cord trauma, neuroanesthesia adjunct, HIV-dementia and the like. Disorders of the peripheral nervous system include diabetic peripheral neuropathy and traumatic nerve damage. Peripheral organ disease includes atherosclerosis (both diabetic and spontaneous), chronic obstructive pulmonary disease (COPD), pancreatitis, pulmonary fibrosis due to chemotherapeutic agents, angioplasty, trauma, bums, ischemic bowel disease, wounds, ulcers and bed sores, lupus, ulcerative colitis, organ transplantation, renal hypertertsion, overexertion of skeletal muscle, epistaxis (pulmonary bleeding), autoimmune conditions, such as systemic lupus (erythematosus), multiple sclerosis and the like; and inflammatory conditions, such as inflammatory bowel disease, rheumatoid arthritis, septic shock, erythema nodosum leprosy, septicemia, uveitis, and the like. With regard to these disease classifications, it will be appreciated by those skilled in the art, that some disease conditions may be classified as, for example, both autoimmune and inflammatory conditions, such as multiple sclerosis and the like.

Other conditions associated: with excessive oxidation of proteins or lipids that can be treated include undesirable or altered oxidation of low density lipoprotein, and dysfunction from exposure to radiation, including x-ray, ultraviolet, gamma and beta radiation, and cytotoxic compounds, including those used for chemotherapy for cancer and viral infections.

Accordingly, in one of its method aspects, this invention provides a method for treating a patient with an acute central nervous system disorder, said method comprising administering to said patient a pharmaceutical composition comprising a pharmaceutically acceptable carrier and an effective acute central nervous system disorder-treating subject hydroxylamine. In a preferred embodiment of this method, the acute central nervous system disorder treated is stroke.

In another of its method aspects, this invention provides a method for treating a patient with an acute cardiovascular disorder, said method comprising administering to said patient a pharmaceutical composition comprising a pharmaceutically acceptable carrier and an effective acute cardiovascular disorder-treating amount of a subject hydroxylamine. In a preferred embodiment of this method, the acute cardiovascular disorder treated is cardiac infarction.

In still another of its method aspects, this invention is directed to a method for treating a patient with a neurodegenerative disease which method comprises administering to said patient a pharmaceutical composition comprising a pharmaceutically acceptable carrier and an effective neurodegenerative disease-treating amount of a subject hydroxylamine. Additionally, this invention is directed to a method for preventing the onset of a neurodegenerative disease in a patient at risk for developing the neurodegenerative disease which method comprises administering to said patient a pharmaceutical composition comprising a pharmaceutically acceptable carrier and an effective neurodegenerative disease-preventing amount of a subject hydroxylamine. In preferred embodiments of this invention, the neurodegenerative disease treated and/or prevented in the above methods is Alzheimer's disease, Parkinson's disease, HIV dementia, a dopamine-associated neurodegenerative condition and the like.

In yet another of its method aspects, this invention is directed to a method for treating a patient with an autoimmune disease which method comprises administering to said patient a pharmaceutical composition comprising a pharmaceutically acceptable carrier and an effective autoimmune disease-treating amount of a subject hydroxylamine. This invention is also directed to a method for preventing the onset of an autoimmune disease in a patient at risk for developing the autoimmune disease which method comprises administering to said patient a pharmaceutical composition comprising a pharmaceutically acceptable carrier and an effective autoimmune disease-preventing amount of a subject hydroxylamine. In preferred embodiments of this invention, the autoimmune disease treated and/or prevented in the above methods is systemic lupus, multiple sclerosis and the like.

In still another of its method aspects, this invention is directed to a method for treating a patient with an inflammatory disease which method comprises administering to said patient a pharmaceutical composition comprising a pharmaceutically acceptable carrier and an effective inflammatory disease-treating amount of a subject hydroxylamine. Additionally, this invention is directed to a method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a subject hydroxylamine. In preferred embodiments of this invention, the inflammatory disease treated and/or prevented in the above methods is rheumatoid arthritis, septic shock, erythema nodosum leprosy, septicemia, uveitis and the like.

In another aspect this invention provides a method for treating a patient suffering from a condition characterized by progressive loss of nervous system function due to mitochondrial dysfunction. This method involves administering to the patient with loss of central nervous system function an effective amount of one or more of the pharmaceutical compositions just described.

In each aspect, the invention may be implemented by a first diagnostic step, e.g. determining that the patient is suffering from, subject to, or predisposed to a target disease or condition followed by prescribing and/or administering to the patient a subject hydroxylamine, optionally followed by a evaluation/confirmation/prognosis step, e.g. determining an effect of the treatment, such as an amelioration of symptom of a targeted disease or condition or an indicator thereof.

Administration

The subject compositions may be formulated for administration by any route, including without limitation, oral, buccal, sublingual, rectal, parenteral, topical, inhalational, including itnranasal, injectable, including subcutaneous, intravenous, intramuscular, etc., topical, including transdermal, etc. The subject compositions are administered in a pharmaceutically (including therapeutically, prophylactically and diagnostically) effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

Intravenous dose levels for treating acute medical conditions range from about 0.1 mg/kg/hour to at least 10 mg/kg/hour over a period of from about 1 to about 120 hours and especially 24 to 96 hours. Preferably, an amount of at least about 0.2 mg/kg/hour is administered to the patient. A preloading bolus of from about 10 mg to about 500 mg may also be administered to achieve adequate steady state levels. While intravenous administration is preferred for acute treatments, other forms of parenteral administration, such as intramuscular injection can be used, as well. In such cases, dose levels similar to those described above may be employed.

Another acute condition which can be advantageously treated with the hydroxylamines of this invention is acute oxidative damage to the cardiovascular system, such as the damage which occurs in a patient who has suffered a cardiac infarction or the like. When treating such a condition, a pharmaceutical composition comprising a hydroxylamine is administered parenterally, e.g. intravenously, at doses similar to those described above for stroke and other acute CNS conditions.

As discussed above, the compounds described herein are suitable for use in a variety of drug delivery systems. Injection dose levels for treating neurodegenerative, autoimmune and inflammatory conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.02 to about 50 mg/kg of hydroxylamine, with preferred doses each providing from about 0.04 to about 30 mg/kg and especially about 1 to about 10 mg/kg.

When used to prevent the onset of a degenerative condition, such as a neurodegenerative, autoimmune or inflammatory condition, the hydroxylamine compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition. When used prophylactically, a pharmaceutical composition comprising a hydroxylamine is administered orally to the predisposed patient. The doses for this oral therapy will typically be the same as those set forth above for treating persons suffering from the neurodegenerative, autoimmune or inflammatory condition.

The compounds of this invention can be administered as the sole active agent or they can be administered in combination with other agents, including other active hydroxylamine compounds.

The following synthetic and biological examples are offered to illustrate this invention and are not to be construed in any way as limiting the scope of this invention.

EXAMPLES

Example 1

Synthesis of N-Isopropylhydroxylamine.

Acetic acid (10.8 g) was added to a cooled solution of 2-nitropropane (5.35 g) and zinc dust (5.89 g) in 95% ethanol (350 mL) at such a rate to maintain the temperature below 10 degree. C. The reaction was stirred for three hours and the solvent removed in vacua. The residue was extracted three times with dichloromethane. The combined extracts were dried over magnesium sulfate, filtered, and solvent stripped. The crude hydroxylamine product was used without further purification. Other hydroxylamines may also be prepared by this procedure.

Example 2

Synthesis of Hydroxylamines By Reduction of Oximes

Various hydroxylamines were prepared according to the procedures of R. F. Borch et al., J. Amer. Chem. Soc., 1971, 93(3):2897 from the corresponding oxime. Specifically, a 3-necked round bottom flask equipped with a stirring motor, a pH meter probe and an addition funnel is charged with a solution of the oxime in methanol (ca. 0.4M). To the stirring solution is added 0.68 equivalents of $NaBH_3$ CN in portions. The addition funnel is filled with 4M HCl in MeOH. The amount of the acid solution prepared should be roughly ¾ of the volume of MeOH used to dissolve the oxime. The HCl solution is then added slowly to the oxime until pH comes down to about 4 and stabilizes at that value. The solution is then allowed to stir at ambient temperature for ca. 4 hours. HCl is added as necessary to keep the pH at 4. (A small sample can be periodically removed and worked-up to determine if the reaction is complete). When the reaction is complete, the solution is decanted into a 1-necked round bottom flask and MeOH is removed in vacua. (While removing the methanol by rotoevaporation, the solvent trap should be filled with NaOH (1 eq.) to quench HCN stripped off with MeOH). After the methanol has been removed, the residue is dissolved in water and extracted with methylene chloride (4.times.). The organic phases are combined, dried over MgSO.sub.4 and stripped to dryness to provide the hydroxylamine product (as determined by NMR and DSC).

Example 3

Synthesis of N-Cyclohexylhydroxylamine

N-Cyclohexylhydroxylamine hydrochloride (commercially available from Aldrich, 1001 West Saint Paul Avenue, Milwaukee, Wis. 53233 U.S.A.) was suspended in ether (about 200 mL of ether for 6 grams of the hydroxylamine salt) and extracted three times with 5% NaOH in brine. The organic phase (white fluffy crystals of N-cyclohexylhydroxylamine suspended in ether) was transferred to a round bottom flask and the ether was removed in vacuo. The resulting crystals were dried under a high vacuum for about 20 min. to afford the title compound.

Example 4

Treatment of Acute CNS Disorders

In this example, the ability of subject hydroxylamines to reduce the infarct volume in an in vivo stroke model is demonstrated. A rat permanent middle cerebral artery occlusion (MCAO) model is used to determine stroke treatment efficacy. MCAO is a representative model of acute CNS disorders. See, for example, M. D. Ginsberg et al., "Rodent Models of Cerebral Ischemia" (1989) Stroke, 20:1627–1642. In this stroke model, the middle cerebral artery is permanently occluded via cauterization to produce a focal stroke. The hydroxylamines are then administered as a 10 mg/kg i.v. bolus dose three hours post MCAO through a catheter surgically implanted in the jugular vein. Two days post MCAO, the rats are sacrificed and the extent of brain damage assessed using tetrazolium staining (TTC staining) followed by computer image analysis to quantitate infarct volumes, i.e., the regions of dead tissue. The mean infarct volume for rats treated with the test compound is significantly less than the mean infarct volume for control rats not treated with the hydroxylamine. Thus, the hydroxylamines can reduce the mean infarct volume of a stroke when administered three hours post stroke compared to controls.

Example 5

Inhibition of A.β Beta-Pleated Sheet Formation

The deposition of amyloid β-peptide (Aβ) is associated with the development of Alzheimer's disease. See, for example, G. G. Glenner et al. (1984) Biochem. Biophys. Res. Commun., 120:885–890; and R. E. Tanzi (1989) Ann. Med., 21:91–94. Accordingly, compounds which effectively disrupt the formation of Aβ(1–40) or Aβ(1–42) beta-pleated sheets are potentially useful for preventing and/or reversing such amyloid deposits. Thioflavin T (ThT) is known to rapidly associate with beta-pleated sheets, particularly the aggregated fibrils of synthetic Aβ(1–40). This association gives rise to a new excitation maximum at 440 nm and to enhanced emission at 490 nm. In this experiment, the ability of the subject hydroxylamines to inhibit the association of ThT with synthetic Aβ(1–40) or Aβ,(1–42) is demonstrated by measuring changes in fluorescence.

The experiments are performed using a CytoFluor II fluorescence plate reader having the following parameters: Filters (Excitation and Emission)=440 nm/20 and 490 nm/40; Gain=75; Cycle to Cycle Time=30 min; Run Time=720 min (24 cycles) or dependent on exp. design; Plate=96 well. Into each well is aliquoted 95 $\mu$L of ThT (3 $\mu$M) prepared in PBS (pH 6.0), 2 $\mu$L of the compound to be tested (10 $\mu$M) prepared with 0.05% of methylcellulose in PBS (pH 6.0), and 3 $\mu$L of A$\mu$(1–40)(3 $\mu$g) prepared with dH$_2$O. The fluorescence measurement begins when the Aβ(1–40) is added and continues for a total of 12 hours. The percent inhibition of beta-pleated sheet formation is calculated from the relative fluorescence unit difference between aggregation in the presence and in the absence of the test compounds. The data show that compounds prepared in Examples 1, 2 and 3 above inhibit Aβ(1–40) beta-pleated sheet formation compared to the controls. In experiments conducted in a similar manner using Aβ(1–42) instead of Aβ(140), the compounds similarly inhibited Aβ(1–42) beta-pleated sheet formation compared to the controls.

Example 6

Protection Against Aβ(2535)-Induced Neuronal Cell Loss

Patients with Alzheimer's disease are known to suffer a progressive loss of neuronal cells. See, for example, P. J. Whitehause et al., (1982) Science, 215:1237–1239. This experiment demonstrates the ability of subject hydroxylamines to protect against Aβ(25–35)-induced neuronal cell loss. Sprague Dawley rat hippocampus of 18-day-gestation embryos are excised and then dissociated by trituration to prepare primary neuronal/astrocyte cultures. Cells (3×10) are plated on 35 mm poly-D-lysine-coated plates containing Eagle's minimum essential medium supplemented with 10% fetal bovine serum. After 3–5 hours, the original medium is removed and replaced with 1 mL of fresh medium. Cultures are maintained at 37° C. in a 5% CO$_2$/95% air humidified incubator.

To the cells (7 DIV) is added 30 $\mu$M of A$\mu$(25–35) dissolved in dH$_2$O (stored at −20° C.) and 100 $\mu$M of a test compound (e.g., a compound of Example 1, 2 and 3 above) in 1% methylcellulose. Controls are also conducted without the test compound. The percentage of morphologically viable neurons is determined counting the number of viable neurons after 96 hours treatment compared to the number of neurons before treatment in the same premarked culture regions (three regions/culture, n=6). The data show that the hydroxylamines reduced Aβ(25–35)-induced neuronal cell loss compared to the controls. In experiments conducted in a similar manner using Aβ(1–40) instead of Aβ(25–35), the compounds prepared in Example 1–3 above also reduce Aβ(1–40)-induced neuronal cell loss compared to the controls.

Example 7

Reduction of Inflammation

In Alzheimer's disease, stroke and multiple sclerosis, researchers have implicated an inflammatory response in the etiology of the disease. See, for example, P. S. Aisen et al., (1994) Am. J. Psychiatry, 151:1105–1113; D. W. Dickson et al., (1993) Glia, 7:75–83; and S. D. Yan et al., Proc. Natl. Acad. Sci. USA, 94, 5296 (1997). This response has been modeled in cell culture by utilizing various factors to simulate the inflammatory response. Such factors include lipopolysaccharide (LPS), an agent known to cause the expression of nitric oxide and other cytokines; and interferon γ(INF-γ), another agent implicated in the inflammatory/cytokine response. This example demonstrates the ability of subject hydroxylamines to reduce the inflammation caused by LPS and INF-γ.

In this experiment, the cell culture system is composed of E16 rat pure cortical neuronal cells (treated with 10 μM Ara C to retard astrocyte growth) that are plated on a confluent bed of two week old cortical glial cells prepared from the cortices of 1 day old rat pups and allowed to grow for one week. To these cells is added LPS (20 μg/mL), IL-1β(40 mg/pg/mL), and INF-γ(200 U/mL), either with or without 100 μM of the test hydroxylamine. Two days later, cell viability was assessed using the lactate dehydrogenase (LDH) assay to monitor cytosolic protein leakage due to cell membrane damage. The results show that the hydroxylamines reduced the inflammation caused by LPS and INF-γ compared to the control.

Example 8

Reduction of μ-Amyloid-Induced Increased Cytokine Release.

This experiment demonstrates the ability of the hydroxylamines to reduce the ,β-amyloid-induced increased release of cytokines, such as interleukin- 1β(IL- 1). THP- 1 cells, a human monocyte cell line from American Type Culture Collection, are grown in RPMI-1640 medium plus 10% fetal bovine serum (FBS, not heat-inactivated) in T-flasks. The medium is changed every two days by spinning down (800 rpm, 5 minutes) the cells and added the same fresh medium. Alternatively, the cultures are maintained by the addition of fresh medium. The cultures are maintained at a cell concentration ranging from between $1 \times 10^5$ and $1 \times 10$ cells/mL. Because sera may contain unknown factors which can affect macrophage/monocyte IL-1 production, the FBS is reduced to 5% for 24 hours. The FBS is further reduced to 2% over two days prior to starting each experiment. The cells are collected by centrifugation and resuspended to 2% FBS. Cell numbers are calculated and cells plated on 24-well plates ($3 \times 10^5$ cells/0.6 mL/well). Cells are then treated with LPS (0.5 μg/ml or 0–10/g/ml for LPS dose-response experiments) alone or in combination with Aβ peptides (5 μM or 0.05–5 μM for dose-response experiments). When determining the effect of the hydroxylamines on cytokine release, 100 μM of the hydroxylamine is added with the LPS and Aβ025–35 and this mixture incubated for 48 hours prior to performing ELISA.

IL-1β secretions into medium by LPS-stimulated THP- 1 cells, in the presence or absence of amyloid peptides and a test compound, are assayed with a commercially available ELISA kit (R & D Systems). Briefly, a microtiter plate coated with a murine monoclonal antibody to human IL-1β is supplied by the manufacturer. Standards and samples are pipetted into the wells and any IL-1β present bound by the immobilized antibody. Unbound proteins are washed away and a horseradish peroxidase-linked polyclonal antibody specific for IL-1β added to the wells to "sandwich" the IL-1β bound in the initial step. After washing to remove any unbound antibody-enzyme reagent, a substrate solution (1:1 hydrogen peroxide—tetramethylbenzidine, v/v) is added to the wells and color developed in proportion to the amount of IL-1β bound in the initial step. Color development is stopped with 2N sulfuric acid and the optical density of the standard and the test samples measured at 450 nm. The amounts of IL-1β present in the samples are calculated based upon a standard curve. Assays are run in quadruplicate wells. The data show that the hydroxylamines reduce the β-amyloid-induced increased release of interleukin-1β compared to the controls.

Example 9

Reduction of Locomotor impairment Due to Aβ-Peptide.

This experiment demonstrates the ability of the hydroxylamines to reduce the in vivo impairment of animals treated with Aβ-peptide. Male Sprague-Dawley rats (250–400 g) are given an ipsilateral injection of 20 μg of Aβ (25–35) into their substantia nigra. Prior to the injection, the rats are fasted overnight and then each received an oral treatment of the hydroxylamines (prepared in Examples 1, 2 and 3 above, 10–100 mg/kg) dissolved in aqueous 1% methyl cellulose or the vehicle alone, one hour before and three hours post the Aβ-peptide stereotaxic injection. One week after treatment, the rats are dosed s.c. with 0.5 mg/kg apomorphine (dissolved in 0.1% vitamin C in isotonic saline) and the circling reflex monitored using a Rotorat computerized behavioral monitoring apparatus for the time period between 15 and 30 minutes of being placed in the arena. Impairment of the animals due to Aβ-peptide is determined by measuring the number of rotations over the 15 minute period. A higher number of rotations per period indicates more physical impairment. The results show that the hydroxylamines reduced the number of rotations per period and hence, the locomotor impairment, of rats injected with Aβ(25–35) compared to Aβ(25–35)-treated controls.

Example 10

Reduction of Spatial Learning Deficit

This experiment demonstrates the ability of the hydroxylamines to reduce spatial learning deficiencies in vivo. Treatment of rats with N-nitro-L-arginine, a nitric oxide synthase inhibitor, is known to cause a deficit in spatial learning. See, for example, G. A. Bohme et al., (1993) PNAS, 90:9191–9194. Rats treated with N-nitro-L-arginine wander aimlessly throughout their enclosure whereas untreated rats spend most of their time in the quadrant in which they are initially placed and stay away from the open area in the middle of the enclosure. This N-nitro-L-arginine-induced spatial learning deficit is used as a model for learning deficits caused by Alzheimer's disease and other dementias.

In this experiment, 10 mg/kg of a hydroxylamine or a control are administered 30 min before each of nine doses of N-nitro-L-arginine (100 mg/kg. iip.). The results show that rats dosed with N-nitro-L-arginine wander equally around the perimeter of the enclosure and readily cross the center of the field. In contrast, rats treated with the hydroxylamines show a preference for the area of the enclosure into which they were first placed and rarely cross the center of the enclosure. This behavior is essentially the same as rats treated with a saline control (i.e., without N-nitro-L-arginine). These results demonstrate that the hydroxylamines prevent the spatial learning deficit caused by N-nitro-L-arginine.

Example 11

Prevention of MBP-Induced Experimental Allergic Encephalomyelitis

Multiple sclerosis (MS) is a chronic inflammatory CNS disorder caused by demyelination in the brain and spinal cord. The disease is characterized by progressive CNS dysfunction, including muscular weakness, tremor, incontinence, ocular disturbances, and mental dysfunction, with remissions and exacerbations. At present, the only treatment for MS is physical therapy.

Experimental allergic encephalomyelitis (EAE) induced by injection of myelin basic protein (MBP) or MBP peptide fragments is reported to be a useful model for MS. See, for example, D. E. McFarlin et al., "Recurrent Experimental Allergic Encephalomyelitis in the Lewis Rat," The Journal of Inmunology, 113(2): 712–715 (1974). This experiment demonstrates the ability of the hydroxylamines to prevent MBP-induced EAE.

Acclimated female Lewis rats, (Harlan; 200–250 g) are used in this experiment since this strain of rat is genetically highly susceptible to EAE. In the experiment, 100 mg/kg of the hydroxylamines (prepared in Examples 1, 2 and 3 above) or a vehicle alone (control) is administered po once a day from days 4 to 18. On day 1, the rats receive an injection of 100 µg of MBP peptide, from guinea pig brain, plus 500 pg of H37RA Mycobacterium in 0.10 ml complete Freund's adjuvant divided equally between the two hind foot-pads.

The rats are evaluated on a 0–6 scale every day after day 7 until day 18 (effects usually begin day 10 and peak day 15). See E. Heber-Katz, "The Ups and Downs of EAE," International Reviews Immunology, 9: 277–285 (1992). These results show that the hydroxylamines completely counteracted the effect of MBP in this test.

Example 12

Prevention of Weight Loss

Animals exposed to MBP or MBP peptide exhibit significant weight loss as compared to controls exposed to Freund's adjuvant alone. To determine if the hydroxylamines prevented such weight loss, the animals in the EAE model described in Examples 1, 2 and 3 above were weighed daily. The results show that those animals receiving the hydroxylamines exhibit normal or above normal weight gain whereas the animals receiving MBP without the hydroxylamines showed serious weight loss.

Example 13

Reduction of Learning Deficit in Autoimmune Mice

This experiment demonstrates the ability of the hydroxylamines to reduce learning deficiencies in autoimmune mice. Male MRL/MpJ controls and Fast mutation mice were either dosed orally with 1% methylcellulose ("MC") or with 100 mg/kg of the hydroxylamines (prepared in Examples 1, 2 and 3 above, "test compound") in 1% methylcellulose for 9–10 weeks. Following dosing, animals of approximately 4 months of age are tested in an active avoidance T-maze. In the one day test, animals are analyzed for acquisition to avoid shock within the first five trials of the test. The data reveal that animals administered the hydroxylamines show a 50% protection in acquisition learning deficit compared to Fas mutated animals receiving only 1% methylcellulose.

Example 14

Comparing In Vivo the Efficacy of Subject Hydroxylamines, PBN, and Two Monosulfonate PBN Compounds as Agents for Protecting Against Neuron Loss Following Brain Ischemia and Reperfusion Injury The test procedure is that reported by W. Cao, J. M. Carney, A. Duchon, R. A. Floyd and M. Chevion as "Oxygen free radical involvement in ischemia and reperfusion injury to brain, Neuroscience Letters, 88 (1988), 233. In the experiments a test compound is administered to groups of six gerbils i.p. as a single dose 30 min before 5 min bilateral carotid occlusion. The density of neuronal nuclei in a 100 micron is measured. Two controls are present—controls which receive no test compound and controls which receive no test compound and no brain ischemia. The compounds of the invention show advantages as compared to the prior art compounds. These results show a clear increase in potency for neural protection for the subject hydoxylamines compared to PBN and two closely related analogs and less in toxicity compared to PBN.

Example 15

Comparing the Subject Hydroxylamines to PBN and Two Sulfonate Analogs in Post-ischemia Treatment The general method described above is used but the test compounds are administered i.p. as a single dose 30 min after reperfusion following 5 min ischemia. The results show that the subject hydroxyamines again more potent at low doses and more potent and less toxic at high doses.

Example 16

Comparing the Subject Hydroxylamines With PBN to Determine the Relative Effectiveness for Protection of Neuronal Loss when Administered i.v. 60 min after Reperfusion Onset Following 5 min Ischemia in Gerbils Using the General Test Method Described Above The results illustrate that the subject hydroxylamines are of significantly greater therapeutic benefit in a clinical treatment setting following injury to the brain. Neither PBN nor the subject hydroxylamines have an effect on neuronal density in control gerbils without brain injury.

Example 17

Brain Injury can Manifest Itself as Behavioral Changes

In this experiment, young adult (3–4 months of age) gerbils are tested to determine their ability to perform an 8-arm maze test 24 hours following an ischemic event as described above As compared to nonischemic animals, when untreated they committed many more errors. PBN and subject hydroxyamines are administered to some of the test animals. Gerbils treated with high doses of the hydroxylamines have error levels indistinguishable from those of nonischemic animals. PBN is less effective. This shows that subject hydroxylamines can protect against the loss of temporal/spatial short term memory following ischemia (24 hours post) errors in 8-arm radial maze test of young gerbils following 5 min ischemia.

Example 18

The Ability of the Subject Hydroxylamines to Reduce Infarct Volume Following an Ischemic Event While PBN and the hydroxylamines are both effective at low doses, at high doses hydroxylamines gave the best protection and PBN was toxic.

Example 19

In this study, subject hydroxylamines and PBN are compared for their ability to impart lethality protection (% survived) in aged gerbils (18–24 months of age, n=12/group) from 10 min ischemia when given 30 min before ischemia. The hydroxylamines are superior at all dose levels and achieve complete protection at high levels while PBN is only partially effective.

Example 20

An important advantage of the subject hydroxylamines as compared to PBN, is its markedly diminished toxicity. Acute lethality in C57BL/6L mice is determined based upon varying sizes of single i.p. doses of hydoxylamine. PBN shows significant toxicity at 560 mg/kg dose levels. The hydroxlamines show no toxicity at doses nearly twenty times as great.

Example 21

Another undesirable systemic effect which has been observed in vivo with nitrone radical traps is a depression in body temperature. This toxicity can have serious health consequences and also can complicate diagnosis of other conditions. The subject hydroxylamines are administered to mice and gerbils at levels as high as 1000 mg/kg with no measurable temperature decrease. In contrast, PBN gives up to an 8° C. decrease in body temperature at a does of only 500 mg/kg.

Example 22

Hydroxylamines effectiveness in the treatment of conditions characterized by protracted low grade oxidative stress upon the central nervous system and gradual progressive central nervous system function loss by effectiveness in a model for Alzheimer's disease ("AD"). Studies have demonstrated that there is an age-associated increase in protein oxidation and loss of enzyme activities in the brain of aged individuals. Tissue cultures of fibroblasts from aged individuals and red blood cells of different ages both show an exponential increase in protein carbonyl content (a measure of protein oxidation) and a decrease in marker enzyme activities. Brain protein oxidation progressively increases over the life span of the individual. The role of abnormal amyloid precursor peptide processing and metabolism in AD has also been explored in a number of different models. In vitro studies using embryonic hippocampal neuronal and neuronal/glial cultures have demonstrated that βAP 1–40 produces cytotoxicity over an extended period of co-incubation. When this peptide is infused into rat brains, lesions are produced. Some of the proposed breakdown fragments of βAP are also neurotoxic, e.g. PAP (25–35). The neurotoxicity appears to be both mediated via glutamate receptors, and also by non-glutamate receptors mechanisms. Confocal microscopy studies of neuronal cultures have demonstrated that exposure to βAP (1–40) results in oxidative stress .

It has been demonstrated that βAP fragments can directly inactivate glutamine synthetase (GS) and creatine kinase (CK) in tissue extracts and in cultured hippocampal neurons and glia. While the hydroxylamines and PBN each show the ability to protect GS and CK against the effects of βAP fragments, the hydroxyamines give complete protection and in fact can at least partly reverse the effects of oxidation. In contrast, PBN's effectiveness is quite limited as it asymptotically levels out at a substantially incomplete level of protection.

Example 23

The effectiveness of the subject hydroxylamines in preventing central nervous system damage caused by stroke. Rat focal ischemia results show the efficacy of subject hydroxylamines in a rat focal ischemia model. In this model, Sprague Dawley rats (200–300 g) undergo a permanent middle cerebral artery occlusion (MCAO) to induce a focal stroke. Subject hydroxylamines are administered after the permanent occlusion as first an intraperitoneal (i.p.) bolus dose and then by intravenous (i.v.) continuous infusion during the remaining time up to 24 hours post stroke. The doses used were either 100 mg/kg, i.p., followed by 4.2 mg/kg/hr, i.v., or 10 mg/kg, i.p., followed by 0.42 mg/kg/hr, i.v. The rats are sacrificed 3 days post stroke, the tissue processed histologically using triphenyltetrazolium staining techniques, and the infarct volume, the area of total cell necrosis, quantitated using image analysis. The results of these experiments demonstrate that subject hydroxylamines provide significant protection, approximately 70%.

Example 24

Evaluating the ability of the subject hydroxylamines to ameliorate oxidation-caused side effects of anticancer therapy. Adriamycin is a widely used anticancer agent. It is known to be very effective but it is also known to have serious side effects arising from its tendency to cause oxidative damage. These side effects include causing serious levels of cardiac damage at high dose levels. These side effects have often limited the use of this agent or limited the dose levels that can be employed to levels which are below those desired for maximum antineoplastic disease effectiveness.

Experiments demonstrate that the subject hydroxylamines are effective at reducing the side effects of anticancer agents such as adriamycin and permitting higher dose levels of adriamycin to be tolerated by animals. C57BL/6J and DBA/2J male mice (35–40 g) are tested for the acute lethal effects of adriamycin and the prevention of acute lethality by pretreatment doses of subject hydroxylamines. Mice are injected i.p with either saline or subject hydroxylamines 30 minutes prior to administration of adriamycin. The acute lethality of adriamycin ranges from 10 to 30 mg/kg. The $LD_{50}$ for adriamycin in these tests was found to be 25 mg/kg in both mouse strains. Hydroxylamines doses up to 300 mg/kg, without adriamycin treatment, have no effect on survival in the two mouse strains. Pretreatment with 30 and 100 mg/kg of hydroxylamines produces dose related shifts in the adriamycin lethality dose effect curve. A dose of 100 mg/kg of subject hydroxylamines produces a 5-fold shift to the right (in the direction of reduced lethality). Thus, the combination of subject hydroxylamines with adriamycin results in a marked increase in the maximally tolerated dose. These higher doses are in the range that would effectively kill multi-drug resistant tumors.

Comparative Tests. PBN pretreatment results in a slight shift to the right in the adriamycin does-effect curve. While the subject hydroxylamine dosages can be increased to 300 mg/kg in combination with adriamycin, there is an upper limit for this combination with PBN. A dose of PBN of 100 mg/kg produces slight sedation and 300 mg/kg yielded marked sedation and some combined toxicity (10–20% lethality). Hydroxylamines/adriamycin does not produce any combined toxicity at doses of hydroxylamine of up to 300 mg/kg.

Example 25

Safety Testing

The subject hydroxylamines and PBN are tested for their acute toxicity in male Sprague Dawley (200–300 g) rats. The compounds are administered at 1000 mg/kg, i.p., to groups of 6 rats. After 3 days lethality is assessed. Hydroxylamines causes no lethality, while PBN is lethal to 5 of the 6 rats used in this test. These data confirm the gerbil data in that the hydroxylamines have higher safety than PBN.

Example 26

Delaying Senescence: Detailed Experimental Protocols

This example shows that N-t-butyl hydroxylamine, a hydrolysis product of β-phenyl-N-t-butyl nitrone, delays senescence in IMR90 human lung fibroblasts. The ability of N-t-butyl hydroxylamine to exert this effect at concentrations much lower than that used for PBN together with increased potency of PBN preparations with longer storage time suggests that this decomposition product mediates PBN's purported actions on IMR9O cells. Benzaldehyde was without effect and in high concentrations was toxic to the cells. Related N-hydroxylamines, N-benzyl hydroxylamine and N-methyl hydroxylamine, have also been found to be active.

Materials-N-t-butyl hydroxylamine, N-benzyl hydroxylamine, N-methyl hydroxylamine (and the corresponding O-hydroxylamines), nitroso-tert-butane, octanesulfonic acid and methanesulfonic acid (MSA) were purchased from Aldrich (Milwaukee, Wis.). Cytochrome c (cyt c), Rho123 and xanthine, NADP, fluorocitrate, isocitrate dehydrogenase (IDH) and PBN were from Sigma (St. Louis, Mo.). Xanthine oxidase was from Boehringer-Mannheim (Indianapolis, Ind.). Aldehyde reactive probe was from Dojindo (Kumamoto, Japan). DCFH was from Molecular Probes (Eugene, Oreg.). DAPER(N,N'-bis(3,3'-(dimethylamino) propylamine)-3,4,9, 10-perylene-tetra carboxylic diimide was from Pierce (Rockford, Ill.). The ABC kit was from Victor labs (Burlington, Calif.). The DNA isolation QIAamp kit was from QIAgen (Valencia, Calif.).

Cultivating IMR90 cells in culture—Normal human epithelial fibroblasts (IMR90) cells were obtained from the Coriell Institute for Medical Research at a population doubling level (PDL) of 10.85. The PDLs were calculated as $\log_2(D/D_o)$, where D and $D_o$ are defined as the density of cells at the time of harvesting and seeding, respectively. Stock cultures were grown in 100 mm Corning tissue culture dishes containing 10 ml of Dulbecco's modified Eagle's medium (DMEM) supplemented with 10% (V/V) fetal bovine serum (Hyclone). Stock cultures were split once a week when near confluence. Cells were harvested by trypsinization for 5 min at 37° C., immediately collected in 5 ml complete DMEM, washed once with 5 ml complete DMEM and incubated for 10–15 min at 37° C. to allow the cells to recover.

To test the effect of hydroxylamines on replicative life span, IMR90 cells were seeded at 0.5×106 per 100 mm dish. N-hydroxylamines (N-t-butyl hydroxylamine, N-benzyl hydroxylamine, N-methyl hydroxyl- amine) were added either individually (final concentration 10 or 100 μM) or in a combination of all three N-hydroxylamines (30 μM each). The cultures were split after 7 days and seeded with fresh medium supplemented with the hydroxylamines described above. In other experiments the medium of the cultures was replaced after 3 days of seeding with fresh medium and with fresh N-hydroxylamines, the split was done as usual after 7 days from seeding. The effect of PBN on life span was tested as in (5).

To determine the effect of $H_2O_2$ on the replicative life span, cells were first seeded with fresh medium with or without N-hydroxylamines (see above) for a week. Next, cells grown with or without N-hydroxylamines were each split into two additional groups and then either; 1) treated with 20 or 30 μM $H_2O_2$ or 2) without treatment with $H_2O_2$.

Analysis of Aconitase activity in tissue culture treated with N-hydroxylamine—Aconitase was measured as described by Gardner et al. (25). Briefly; IMR90 cells were grown with or without N-hydroxylamine as described above. After 12 weeks of treatment the cells were washed twice by cold PBS and scraped from the dishes by cell scraper. The cells (3–4×10$^6$) were collected by centrifugation and resuspended into 200 μl of ice cold 50 mM tris, pH 7.4/0.6 mM $MnCl_2$/20 μM fluorocitrate supplemented with antiprotease mixture (leupiptin, pepstatine and PMSF, 1 μg each). The cells were disrupted by three cycles of sonication for 3–5 sec at low output separated by 1 minute of incubation in ice. Then the lysate was spun at 12000 g for 5 min in 4° C. and the supernatant was used to measure total soluble protein and aconitase activity. In general 60–100 μg of protein are adequate to readily detect aconitase activity as described (25).

Analysis of the age-dependent changes in the steady state level of oxidants and mitochondrial membrane potential in IMR90 cells by FACS—190 cells were trypsinized and resuspended into complete DMEM. For each condition, two tubes were prepared with 1×10$^6$ cells each. Tubes were then spun at 250 g for 10 min at room temperature and supernatant was replaced with 1 ml of Hanks Balanced Salt Solution (HBSS) without $Ca^{++}$ or $Mg^{++}$. Rho123 (20 μl of 525 μM stock; 10.5 μM final concentration) was added to one tube and DCFH (20 μl of 1.25 mM stock; 25 μM final concentration) was added to the other tube. The cells were then incubated in the dark in a water bath at 37° C. for 30 min followed by cell resuspension and centrifugation at 250 g for 10 min at room temperature. The supernatant (500 μl) was removed from each tube and the cells were resuspended in the remaining 500 μl before FACS analysis on a FACSort analyzer (Becton Dickinson, San Jose, Calif.). Cell Quest was used for data acquisition and analysis. The data is reported as the mean of the channel of the fluorescence histogram obtained. Fluorescence output was calibrated with LinearFlow Green Flow cytometry Intensity Calibration Particles (Molecular Probes, Eugene, Oreg.).

Measurement of apurinic/apyrimidinic (AP) sites in IMR90 cells—Briefly, AP sites were measured as follows: IMR90 cells (1–2×10$^6$) in 0.5 ml PBS/5 mM glucose were incubated with 3 mM Aldehyde Reactive Probe (ARP) for 60 min at 37° C. The cells were then collected by centrifugation at room temperature and washed twice with 1 ml PBS. DNA was isolated by the QIAamp blood kit as suggested by the manufacturer. DNA was quantified by Picogreen and 1 μg was transferred into 200 μl of elution buffer (10 mM Tris, pH 8.9), mixed with 14 μl of 5 M NaCl (the mole ratio of NaCl/dNTP should be 25000–30000) and incubated for 60 min at room temperature with 30 μl of freshly prepared avidin-HRP (ABC kit), prepared as described by the manufacturer but with avidin-HRP concentrations diluted 1:3 and the incubation volumes scaled down to 1 ml. The DNA-avidin-HRP complex (DNA-HRP) was separated from unbound avidin-HRP by gently mixing 65 μl of 1 mM DAPER(N,N'-bis(3,3'-(dimethylamino)-propylamine)-3,4,9, 10-perylene-tetra carboxylic diimide) with the DNA and incubated at room temperature for 5 min. The DNA-DAPER precipitate was then collected by centrifugation for 5 min at 12,500 g, and washed twice with 1.5 ml of 0.17 M NaCl/20mM Tris/0.25% Tween-20/1% BSA, pH 8. The precipitate of DNA-HRP was suspended in 500 μl of ice cold 50 mM Na-Citrate, pH 5.3 and sonicated at output 1–2 watts for 5 sec (Sonifier cell Disruptor, model w185D, Branson) and cooled immediately. HRP activity was measured as an indicator of AP sites in DNA-HRP by using the chromogenic ImmunoPure TMB or the fluorogenic QuantaBlu Substrate kits. The background control was established by performing a parallel analysis on calf thymus DNA. The standard curve for AP sites was constructed with 100 ng of DNA standard containing a known amount of uracil suspended in 500 µl of 10 mM $Na_2HPO_4$, pH 7.5. The standard DNA was incubated with 25 µM spermine for 3 min and then with 3 U of uracil-DNA N-glycosylase (UNG) for 20 min at 37° C. to catalyze the removal of uracil residues and generate AP sites. The resulting "AP enriched" DNA was incubated with 3 mM ARP for 45 min at 37° C. The standard DNA-ARP adducts were isolated from unbound ARP by QIAamp columns (without the protease step) and quantified. The number of AP sites were corrected for the loss of DNA during isolation (10–20% loss). The biotinylated DNA was incubated with avidin-HRP and processed as above.

Reduction of cyt $c^{III}$ by superoxide radical—Superoxide radical was generated by the reaction of xanthine (120 µM) with xanthine oxidase (XO, 0.06 U). The reaction was performed at 25° C. in a final volume of 1 ml PBS containing 40 µM cyt $c^{III}$. The reaction was started by the addition of the substrate xanthine (X). N-hydroxylamines were added just before the addition of X. The initial rate of reduction of cyt $c^{III}$ was determined based on the linear change in absorbance at 550 nm.

In order to test the effect of N-hydroxylamines on the spontaneous oxidation of cytochrome c, a complete reduction of cyt $c^{III}$ was achieved by incubating the X/XO system for 4–5 min at 25° C. Auto-oxidation of cyt $c^{II}$ is associated with a decrease in absorbance at 550 nm. Reduced cytochrome c was incubated at 25° C. with or without 2 or 3 mM N-hydroxylamines and the auto-oxidation was followed by spectrophotometer. The rate of reduction of cytochrome c by different concentrations of each N-hydroxylamine was measured by the increase in absorbance at 550 nm.

Measurement of cellular levels of GSH and GSSG in IMR90 cells—Cultivated IMR90 cells ($\approx 3 \times 10^6$) were washed once in cold PBS and resuspended in 200 µl of ice cold MSA (0.2M MSA/0.5mM diethylenetriamine pentaacetic acid, DTPA) and allowed to stand for 10 min at room temperature. Denatured proteins were removed by centrifugation and the supernatant was filtered with 30,000 D MW cut-off Ultrafree filters (Millipore) before injection. Fifty microliters were injected and separated on an HPLC column (3-µm 0.46×15cm Suplecosil LC18-DB, Supelco, Bellefonte, Pa.) with a flow rate of 1 ml/min using a mobile phase consisting of 25mM $NaH_2PO_4$, 5 mM octane sulfonic acid, and 2% acetonitrile, adjusted to pH 2.7 with phosphoric acid (26). An ESA model 5100A Coulochem detector, 5020 guard cell and model 5010 analytical cell combination was used for analysis. Oxidation potentials of 900 mV, 400 mV and 880 mV were used for guard cell, electrode 1 and 2, respectively. Full-scale output was 10 µA and peak areas were compared using commercial GSH and GSSG as standards.

N-t-butyl hydroxylamines, and other N-hydroxylamines delay senescence of IMR90 cells—N-t-butyl hydroxylamine, N-benzyl hydroxylamine and N-methyl hydroxylamine (N-hydroxylamines, scheme 1) at 100 µM (added once per 7 days) delay senescence of IMR90 cells by at least 17–20 PDLs. The concentration of PBN required to achieve nearly a similar gain in PDLs is 8 times higher than N-hydroxylamines (table 1 and (5)).

Table 1. The gain in PDLs of cultured IMR90 cells after continuous cultivation with PBN and N-t-butyl hydroxylamines compared to control untreated cells. IMR90 cells were cultured in the presence of various compounds and PDL followed until senescence. PDL were calculated as described in methods. Data from a representative experiment is shown. NtBHA=N-t-butyl hydroxylamine.

| Treatment | Gain in PDLs |
| --- | --- |
| 800 µM PBN | 14.8 |
| 200 µM PBN | 2.4 |
| 100 µM NtBHA | 19.7 |
| 10 µM NtBHA | 5.8 |

The minimal concentration of N-hydroxylamines required to achieve a gain of 5–7 PDLs above the untreated control was 20 times lower than that for PBN (200 µM) to achieve 2–3 PDLs (table 1 and (5)). For each of the three N-hydroxylamines when IMR90 cells were treated at 25 µM every 3 days, it was twice as efficient as 100 µM every 7 days. None of the N-hydroxylamines tested were toxic at the concentration applied to the cells, as measured by PDL; whereas benzaldehyde, the co-product of PBN hydrolysis, was without effect or toxic at high concentrations. All the N-hydroxylamines, at the concentrations tested, were more effective than PBN in delaying senescence. The N-hydroxylamines studied appear to be equally efficient in delaying senescence, with a variation only when cells are close to senescence (late PDLs).

A simultaneous treatment of the cells with all three of the N-hydroxylamines (30 µM each) yielded results similar to single treatments, delaying senescence by 14–17 PDLs. In contrast, at concentrations equivalent to the N-hydroxylamines, the isomeric O-hydroxylamines (O-t-butyl hydroxylamine, O-benzyl hydroxylamine and O-methyl hydroxylamine) were found to accelerate senescence.

N-t-butyl hydroxylamines, and other N-hydroxylamines delay senescence-dependent change in mitochondria—Senescence-dependent change in mitochondria of IMR90 cells was estimated by Rho123. The Rho123 fluorescence that accumulated in the cells was measured weekly by FACS for a total of at least 8 weeks and plotted against the current PDL (i.e., age of the cells). The age-dependent incorporation of Rho123 in IMR90 is biphasic. This is characterized by a slow and linear increase at early PDLs, followed by a shorter and steeper phase at late PDLs. Linear regression analysis was used to calculate the rate of Rho123 accumulation as a function of PDL (Table 2).

Table 2. Rate of Rho123 accumulation and DCFH oxidation per PDL in IMR90 cells treated with N-hydroxylamines. IMR90 cells were treated with N-hydroxylamines beginning at PDL 24–27. Every week the gain in PDLs was calculated and DCFH and Rho123 accumulation was determined by FACS analysis. The PDL dependent change for each parameter was calculated using linear regression for data obtained of cells cultured between 26–50 PDLs (at least 8–10 points for each treatment). Data from a representative experiment is shown. AFU=arbitrary fluorescence units. NMHA, N-methyl hydroxylamine; NBHA, N-benzyl hydroxylamine; NtBHA, N-t-butyl hydroxylamine.

| Treatment | DCFH, AFU/PDL | Rho123, AFU/PDL |
|---|---|---|
| Control, PBS | 2.18 (0.73) | 31.7 (0.67) |
| NtBHA (100 $\mu$M) | 0.27 (0.32) | 9.3 (0.85) |
| NBHA (100 $\mu$M) | 0.11 (0.08) | 9.7 (0.86) |
| NMHA (100 $\mu$M) | 0.45 (0.3) | 15.3 (0.86) |

| Treatment | GSH | GSSG | GSH/GSSG |
|---|---|---|---|
| Control, PBS | 54.4 ± 5.2 | 0.77 ± 0.06 | 70.6 |
| NtBHA (100 $\mu$M) | 49.5 ± 5.6 | 0.4 ± 0.045** | 123.8 |
| NBHA (100 $\mu$M) | 48.4 ± 3.4 | 0.36 ± 0.015** | 134.4 |
| NMHA (100 $\mu$M) | 52.15 ± 6.7 | 0.38 ± 0.08* | 137.2 |

The regression analysis was based on early PDLs only, late PDLs were not included in the analysis. The increment in accumulation of Rho123 indicates a senescence-dependent change in the mitochondria of IMR90 cells as they become senescent. N-hydroxylamines delay these changes in mitochondria, and the rate of Rho123 accumulation as a function of senescence decreased by 70%, 69%, and 52% for N-t-butyl hydroxylamine, N-benzyl hydroxylamine and N-methyl hydroxylamine, respectively (Table 2).

N-t-butyl hydroxylamines, and other N-hydroxylamines decrease formation of oxidants and oxidative DNA damage in IMR90 cells—The level of oxidants was measured each week by estimating the oxidation of DCFH (27) in the living cells. Measurements of fluorescence of oxidized DCFH were made weekly by FACS for total of at least 8 weeks and plotted against the current PDL (i.e., age of the cells), and a biphasic curve, similar to that seen with Rho123 fluorescence, was observed with DCFH fluorescence. A linear regression analysis was used to calculate the initial linear rate of DCFH oxidation as a function of PDL (Table 2). The regression analysis was based on early PDLs only. Late PDLs were not included in the analysis. IMR90 cells treated continuously with N-hydroxylamines exhibit a slower rate of formation of oxidants compared to control cells. The percent of decrease in the rate of oxidants formation from control are 88%, 95% and 79% for N-t-butyl hydroxylamine, N-benzyl hydroxylamine and N-methyl hydroxylamine, respectively (Table 2). The level of AP sites in DNA can be used as a measure of the level of oxidative damage. IMR90 cells treated simultaneously with the three N-hydroxylamines (30 $\mu$M each) showed a 52% reduction in AP sites compared to PDL matched control cells.

N-t-butyl hydroxylamines and the other N-Hydroxylamines increase the activity of aconitase in IMR90 cells—A 2–3 fold age-dependent decline in the activity of aconitase is seen in old (high PDL) compared to young (low PDL) IMR90 cells. The age-dependent decline in the activity of aconitase to a large extent was prevented when the cells were grown with N-hydroxylamines. The efficiency of protecting aconitase from inhibition was as follows; N-t-butyl hydroxylamine (90%)≧N-benzyl hydroxylamines (75%)>>N-methyl hydroxylamine (17%). This order is comparable to the relative efficiencies for the ability to delay senescence.

N-hydroxylamines increase the GSH/GSSG ratio in IMR90 cells—The three N-hydroxylamines tested improved the glutathione status in IMR90 cells. The GSH/GSSG ratio increased by 75%, 90.4% and 94% for N-t-butyl hydroxylamine, N-benzyl hydroxylamine and N-methyl hydroxylamine, respectively (Table 3).

Table 3. The status of GSH, GSSG and GSH/GSSG in IMR90 cells treated with N-hydroxylamines. IMR90 cells at PDL 24–27 were cultivated with N-hydroxylamines and every week the gain in PDL was calculated. About 3×10$^6$ cells were used to determine GSH and GSSG by HPLC-EC. The range of PDLs included between 26 and 50 PDLs (at least 6 measurements for each treatment).* P<0.02,** P<0.01

The GSH/GSSG ratio increased because of a decrease in the level of GSSG in treated cells compared to untreated cells. No change in the level of GSH was observed between the treated and control groups (Table 3). When the cells were treated simultaneously with the three N-hydroxylamines a similar effect on GSH metabolism was observed.

IMR90 cells treated with N-t-butyl hydroxylamine and N-benzyl hydroxylamine are resistant to hydrogen peroxide—Hydrogen peroxide, applied at low concentrations (20 $\mu$M or 30 $\mu$M in fresh medium) once a week to control IMR90 cells accelerated senescence. The $H_2O_2$-induced senescence was attenuated when these cells were continuously treated with N-t-butyl hydroxylamine, N-benzyl hydroxylamine or both compounds+N-methyl hydroxylamine.

N-Hydroxylamines inhibit reduction of cyt $c^{III}$ by superoxide radical-N-hydroxylamines at relatively high concentrations (5–10 mM) were able to inhibit the reduction of cyt $c^{III}$ by X/XO, a system that generates superoxide radical. The catalytic activity of the enzyme XO was not inhibited by N-hydroxylamines, as judged from the rate of formation of uric acid (the co-product with $O_2^-$) in the presence or absence of N-hydroxylamines (data not shown). Moreover, N-hydroxylamines prevented auto-oxidation of cyt $c^{II}$. N-hydroxylamines were able to reduce cyt $c^{III}$ directly to cyt $c^{II}$, which explains their ability to delay the oxidation of reduced cyt $c^{II}$. The reduction of cytochrome c by N-hydroxylamines was equally efficient under aerobic and anaerobic condition or in the presence of iron chelator (DTPA). A differential ability to reduce cytochrome c was observed for the three different N-hydroxylamines, N-t-butyl hydroxylamine being somewhat less efficient.

In this example, we have demonstrated that the products of PBN or PBN/OH hydrolysis, N-t-butyl hydroxylamine, but not benzaldehyde, delays the replicative senescence of human lung fibroblasts at concentrations 20 times lower than PBN. Thus N-t-butyl hydroxylamine is much more effective than PBN in delaying senescence of IMR90 cells and appears to be the active component in old preparations of PBN. Other N-hydroxylamines tested (not related to PBN, e.g., N-benzyl hydroxylamine and N-methyl hydroxylamine), were also able to delay the senescence of IMR90 cells. Thus, we conclude that the N-hydroxylamine functional group is responsible for their biological activity. On the other hand, although PBN is a spin trap and an antioxidant, none of the well known spin traps or antioxidants studied (ascorbic acid, vitamin E, catalase, 2,2,6,6-tetramethyl-piperidine-1-oxyl (TEMPO) and 4-hydroxy-2,2,6,6-tetramethylpiperidine- 1-oxyl (4-OH-TEMPO) can delay senescence of IMR90 cells as does PBN. These results indicate that the effect of PBN on IMR90 cells is due to N-t-butyl hydroxylamine and not PBN itself.

In order to gain more insight into the effect of N-hydroxylamines on cells, we assessed the status of different cellular parameters in cells that have continuously been grown with medium supplemented with N-hydroxylamines compared to controls. We show that, concomitantly with delayed senescence by N-hydroxylamines, the PDL-dependent formation of oxidants was decreased as estimated by DCFH oxidation (Table 2), and an increase in the GSH/GSSG ratio (Table 3). The age-dependent decay in mitochondria was delayed as estimated by Rho123 accumulation (Table 2) and by the inhibition of the age-dependent decline in the activity of aconitase. The level of AP sites in DNA of cells treated with N-hydroxylamines was also 52% lower than that of the control cells. The increase in the ratio GSH/GSSG by treatment with N-hydroxylamines was due to a decrease in the steady-state level of GSSG, without changing the concentration of GSH. In addition N-hydroxylamines prevented the age-dependent decline in aconitase activity in IMR90. Aconitase is an enzyme essential for the Krebs cycle and highly abundant in mitochondria compared to cytosol (28). Its iron-sulfur cluster is known to be damaged by superoxide radical and ONOO$^-$(25,29,30). The mitochondrial enzyme is more sensitive to inhibition by superoxide radical and oxidative modification compared to the cytosolic enzyme (29,31). These findings indicate that N-hydroxylamines lower the endogenous level of oxidants in mitochondria, thus protecting aconitase and causing less GSH to be oxidized to GSSG. Since aconitase plays an important role in the Krebs cycle, changes in its activity will have a large impact on mitochondrial and cellular metabolic pathways. N-hydroxylamines also protect IMR90 cells from $H_2O_2$-induced senescence, by acting as mitochondrial antioxidants. This is further supported by the 79–95% decrease in the rate of DCFH oxidation in N-hydroxylamine treated cells compared to controls.

PBN has been shown to protect against oxidative damage in different biological models as well at higher concentrations (5,32–34). Interestingly, PBN inhibits formation of hydrogen peroxide at the level of complex I in mitochondrial preparations which suggests a direct interaction with mitochondria in vivo (10). The antioxidative effect of N-t-butyl hydroxylamine can be attributed to a similar, though more efficient, inhibition of superoxide formation by mitochondria in vivo, resulting in less hydrogen peroxide being formed. We studied further the interaction of N-t-butyl hydroxylamine (as representative of primary N-hydroxylamines) with mitochondria in IMR90 cells. Intracellular N-t-butyl hydroxylamine is maintained in the reduced form by mitochondrial NADH and complex I. Since N-t-butyl hydroxylamine is stable to auto-oxidation in a cell free system, this indicates that N-t-butyl hydroxylamine cycles inside the cells between the oxidized and reduced form. Complex I is a mitochondrial site that is implicated in the formation of superoxide radical, indicating that N-t-butyl hydroxylamine interacts with this site to prevent formation of superoxide radical, as with the interaction of PBN with complex I (10).

The age-related increase in oxidative damage to mitochondrial DNA, proteins and lipids is thought to be a major factor in organismal aging (6,35–38). Since mitochondria are assumed to play a major role in the formation of superoxide radical and suggested to contribute to aging, we compared the senescence-dependent changes in mitochondria in control and N-hydroxylamine treated cells. A PDL-dependent accumulation of Rho123 is observed in IMR90 cells, which reflects a senescence-dependent change in mitochondria (Table 2). This change may be due to age-dependent mitochondrial swelling, or changes in the mitochondrial inner membrane that elevates the non-specific binding of Rho123 to this membrane (6,39). Accumulation of Rho123 was also observed in one fraction of isolated hepatocytes from livers of old rats over hepatocytes from young rats (6). When IMR90 cells were grown in medium supplemented with N-hydroxylamine, a 52–70% slower rate of the age-dependent accumulation of Rho123 was observed when compared to control cells. This indicates, in conjunction with the protective effect on aconitase, that N-hydroxylamines interact with mitochondria and delay the senescence-dependent changes to mitochondria. Since mitochondria are a major source for free radical formation, improving the mitochondrial status provides a significant decrease in the level of oxidants in the cells (Table 2).

We also found that cyt $c^{III}$ is reduced directly by N-hydroxylamines independently of oxygen or iron, indicating that superoxide radical is not an intermediate in the process. Reduction of cyt $c^{III}$ by N-hydroxylamines indicates that N-hydroxylamines can interact in vivo with cytochrome c in addition to mitochondrial NADH. Cyclic-N-hydroxylamines/cyclic-nitroxides are recycled by mitochondrial ubiquinol and cytochrome oxidase (22,23), a mechanism of regeneration that may be shared by the primary N-hydroxylamines used in the present study. Our primary data show that mitochondrial NADH is involved in keeping the intracellular N-hydroxylamines in reduced form. N-hydroxylamines (5–10 mM) inhibit the reduction of cyt $c^{III}$ by superoxide radical, which was generated with xanthine/xanthine oxidase. N-hydroxylamines do not inhibit the catalytic activity of xanthine oxidase since the formation of uric acid (obligatory product with superoxide radical) was not inhibited. This indicates that in vivo, primary N-hydroxylamines (or their corresponding nitroxides), react with superoxide radical, as is known for the cyclic-hydroxylamines/cyclic-nitroxides. We find that N-t-butyl hydroxylamine rapidly enters the cells and is concentrated by approximately 5-fold. In order to test the contribution of superoxide scavenging to the mechanism of senescence delay we tested two cyclic-nitroxides as typical non-metal SOD mimics. Both of the cyclic-nitroxides tested (TEMPO and 4-OH-TEMPO) did not delay the replicative senescence of the cells (at 25 $\mu$M) and at high concentrations (100/$\mu$M) were even toxic. This indicates that SOD mimic activity (which gives $H_2O_2$) by itself can not account for the protective effects and senescence delay observed with the primary N-hydroxylamines used in this study. Consequently we conclude that mitochondria are a primary target for N-hydroxylamines due to their ability to slow the senescence-dependent changes to mitochondria, lower oxidants and delay senescence of IMR90 cells.

Nitric oxide was proposed as a product of PBN decomposition and thus was suggested to possess a role in the activity of PBN in vivo. N-t-butyl hydroxylamine has also been shown to be oxidized by UV photolysis to produce nitroso-tert-butane (tNB), which further decomposes to give nitric oxide (11,13). The in vivo evidence for the formation of N-t-butyl hydroxylamine-dependent (or PBN-dependent) nitric oxide has not been demonstrated, and the evidence is circumstantial or based on in vitro experiments (40,41). In order to assess if tNB contributes to the effect of N-t-butyl hydroxylamine on IMR90 cells, the cells were grown in a medium supplemented with tNB. We found that tNB is toxic at 50 $\mu$M, and has no effect on the cells at much lower concentrations (10 $\mu$M). Thus, tNB plays a negligible role in the mechanism underlying the biological effect of N-t-butyl hydroxylamine.

The N-hydroxylamines used in this study all exhibit the ability to delay cellular senescence. Cyclic-N-hydroxylamines ($R_2$NOH) and their respective nitroxides enhance the clinical recovery of damaged brains in closed-head injury (42) and protect against oxidative damage induced by $H_2O_2$ (43) but did not delay cellular senescence. This emphasizes the remarkable feature of the primary N-hydroxylamines as antioxidants. Harman in 1961 (44) reported that HNHOH (hydroxylamine) possesses anticancer activity and delayed senescence in mice. On the other hand O-hydroxylamines which possess a different functional group ($R-O-NH_2$), but the same alkyl groups (and benzyl group) as N-hydroxylamines, do not affect the rate of senescence, the level of oxidants or the changes in mitochondria in IMR90 cells. This further indicates that the N-hydroxylamine functional group (R-NHOH) is involved in the effect of delaying senescence in IMR90 cells. The alkyl and aromatic groups of the primary N-hydroxylamines can affect their oxidation-reduction potential, as is the case with cyclic nitroxides/cyclic hydroxylamines (22). This ratio is also determined by the oxygen status of the cell (24,45). In addition, the alkyl groups and their different hydrophobicities can influence the intracellular location of the N-hydroxylamines.

In summary, the anti-senescence effect of PBN on IMR90 cells can be mimicked efficiently by N-t-butyl hydroxylamine, and other N-hydroxylamines which indicates that the functional compound in the PBN preparation is the N-hydroxylamine rather than PBN itself. Other N-hydroxylamines were also effective in delaying senescence and protecting IMR90 cells. The use of N-hydroxylamine also avoids the benzaldehyde formed when PBN decomposes (41). The low doses of N-hydroxylamine required make them desirable compounds for delaying aging and protecting from oxidative damage. This is the first time that an anti-aging activity has been attributed to a group of chemicals that share a common functional group.

Parenthetical References

1. Oliver, C. N., et al. (1990) *Proc Natl Acad Sci USA* 87(13), 5144–7
2. Carney, J. M., et al. (1991) *Proc Natl Acad Sci USA* 88(9), 3633–6
3. Edamatsu, $R_1$, et al. (1995) *Biochem Biophys Res Commun* 211(3), 847–9
4. Saito, K., Yoshioka, H., Cutler, R. G. (1998) *Biosci Biotech Biochem* 62(4), 792–4
5. Chen, Q., et al. (1995) *Proc Natl Acad Sci USA* 92(10), 4337–41
6. Hagen, T. M., et al. (1997) *Proc Natl Acad Sci USA* 94(7), 3064–9
7. Yue, T. L., et al. (1992) *Brain Res* 574(1–2), 193–7
8. Nakashima, M., et al. (1999) *Free Radic Biol Med* 26(5–6), 722–9
9. Sen, S., and Phillis, J. W. (1993) *Free Radic Res Commun* 19(4), 255–65
10. Hensley, K., et al. (1998) *J Neurochem* 71(6), 2549–57
11. Chamulitrat, W., et al. (1995) *Free Radic Res* 23(1), 1–14
12. Britigan, B. E., et al. (1990) *J Biol Chem* 265(29), 17533–8
13. Chamulitrat, W., et al. (1993) *J Biol Chem* 268(16), 11520–7
14. Dikalov, S. I., et al. (1999) *J Biol Chem* 274(14), 9392–9
15. Gee, P., et al. (1998) *Mutat Res* 412(2), 115–30
16. Gold, L. S., et al. (1997) in *Handbook of Carcinogenic Potency and Genotoxicity Databases* (Gold, L. S., and Zeiger, E., eds), pp. 1–605, CRC Press, Boca Raton, Fla.
17. Zhang, R., Goldstein, S., Samuni, A. (1999) *Free Radic Biol Med* 26(9–10), 1245–52
18. Samuni, A., et al. (1990) *Free Radic Res Commun* 9(3–6), 241–9
19. Samuni, A., et al. (1988) *J Biol Chem* 263(34), 17921–4
20. Krishna, M. C., et al. (1996) *J Biol Chem* 271(42), 26018–25
21. Krishna, M. C., et al. (1992) *Proc Natl Acad Sci USA* 89(12), 5537–41
22. Swartz, H. M. (1990) *Free Radic Res Commun* 9(3–6), 399–405
23. Belkin, S., et al. (1987) *Arch Biochem Biophys* 256(1), 232–43
24. Chen, K., et al. (1989) *Biochemistry* 28(6), 2496–501
25. Gardner, P. R., et al.(1994) *Proc Natl Acad Sci USA* 91(25), 12248–52
26. Lakritz, J., et al. (1996) *J Pharmacol Exp Ther* 278(3), 1408–18
27. LeBel, C. P., Ischiropoulos, H., Bondy, S. C. (1992) *Chem Res Toxicol* 5(2), 227–31
28. Guarriero-Bobyleva, V., et al. (1973) *Eur J Biochem* 34(3), 455–8
29. Yan, L. J., et al. (1997) *Proc Natl Acad Sci USA* 94(21), 11168–72
30. Fridovich, I. (1997) *J Biol Chem* 272(30), 18515–7
31. Williams, M. D., et al. (1998) *J Biol Chem* 273(43), 28510–5
32. Parman, T., Wiley, M. J., and Wells, P. G. (1999) *Nat Med* 5(5), 582–5
33. Butterfield, D. A., et al. (1997) *Proc Natl Acad Sci USA* 94(2), 674–8
34. Kashiwakura, I., et al. (1997) *Res Commun Mol Pathol Pharmacol* 98(1), 67–76
35. Hagen, T. M., et al. (1998) *Proc Natl Acad Sci USA* 95(16), 9562–6
36. Beckman, K. B., and Ames, B. N. (1998) *Physiol Rev* 78(2), 547–81
37. Shigenaga, M. K., et al. (1994) *Proc Natl Acad Sci USA* 91(23), 10771–8
38. Hagen, T. M., Wehr, C. M., and Ames, B. N. (1998) *Ann N Y Acad Sci* 854, 214–23
39. Scaduto, R. C., Jr., and Grotyohann, L. W. (1999) *Biophys J* 76(1 Pt 1), 469–77
40. Saito, K., et al. (1998) *Biol Pharm Bull* 21(4), 401–4
41. Albano, E., et al. (1986) *Biochem Pharmacol* 35(22), 3955–60
42. Zhang, $R_1$, et al. (1998) *Free Radic Biol Med* 24(2), 332–40
43. Twomey, P., et al. (1997) *Free Radic Biol Med* 22(5), 909–16
44. Harman, D. (1961) *Gerontology* 16, 247–54
45. Chen, K., and Swartz, H. M. (1988) *Biochim Biophys Acta* 970(3), 270–7

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A pharmaceutical composition comprising an orally administrable effective unit solid dosage of a primary N-hydroxylamine or a pharmaceutically acceptable salt thereof and substantially free of a nitrone corresponding to the hydroxylamine, wherein the hydroxylamine has the general formula,

NHOHCR₁R₂R₃, wherein $R_1$, $R_2$ and $R_3$ are independently selected from: hydrogen, substituted or unsubstituted (C1–C10) alkyl, alkenyl, alkynyl aryl, oxyl, acyl, carboxyl, amino, nitro, nitroso, oxime, hydrazone, azo, thiol, sulfonyl and halide, wherein the composition is packaged with a label identifying the primary N-hydroxyl amine and prescribing a pharmaceutical use thereof and the use comprises reducing oxidative damage or delaying senescence.

2. A composition according to claim 1, wherein the dosage is from 100 μg to 1 g.

3. A composition according to claim 1, wherein at least one R of $R_1$, $R_2$ and $R_3$ is selected from unsubstituted (C1–C10) alkyl, alkenyl and alkynyl.

4. A composition according to claim 1, wherein at least one R of $R_1$, $R_2$ and $R_3$ is selected from unsubstituted (C1–C18) alkyl, cycloalkyl, alkenyl and alkynyl, and the R is selected from: $CH_3-(CH_2)_{n1}$, $(CH_3-(CH_2)_{n2}-)_2 CH$, $(CH_3-(CH_2)_{n2}-)_3$, cyclopentyl, cyclohexyl, $(CH_2=CH-Ch_2)_{n3}$ and $(CH=C-CH_2-)_{n3}$, wherein n1=1 to 18, n2=1 to 17 and n3=1 to 3.

5. A composition according to claim 1, wherein at least one R of $R_1$, $R_2$ and $R_3$ is selected from hydrogen, unsubstituted (C1–C10) alkyl, alkenyl and alkynyl, and the hydroxylamine is selected from:

N-methylhydroxylamine,
N-ethylhydroxylamine,
N-n-propylhydroxylamine,
N-(n-butyl)hydroxylamine,
N-(n-pentyl)hydroxylamine,
N-(n-hexyl)hydroxlamine,
N-(n-heptyl)hydroxylamine,
N-(n-octyl)hydroxylamine,
N-(n-nonyl)hydroxylamine,
N-(n-decyl)hydroxylamine,
N-(n-dodecyl)hydroxylamine,
N-(n-decahexyl)hydroxylamine,
N-(n-decaoctyl)hydroxylamine,
N-isopropylhydroxylamine,
N-sec-butylhydroxylamine,
N-tert-butylhydroxylamine,
N-cyclohexylhydroxylamine,
N-cyclopentylhydroxylamine,
N-(2-propene)hydroxylamine,
N-(3-butene)hydroxylamine,
N-(2-propyne)hydroxylamine and
N-(3-butyne)hydroxylamine.

6. A composition according to claim 1, wherein at least one R of $R_1$, $R_2$ and $R_3$ is substituted or unsubstituted aryl.

7. A composition according to claim 1, wherein at least one R of $R_1$, $R_2$ and $R_3$ is substituted or unsubstituted aryl, and the R is selected from: mono, di, or tri methyl, methoxy, halo, nitro, amino, hydroxyl and substituted or unsubstituted phenyl, naphthyl, anthryl, phenanthryl, pyridyl, quinolinyl, imidazolyl, benzoxazolyl, pyrrolyl, furanyl, piperidinolyl and tetrahydrofuranyl.

8. A composition according to claim 1, wherein at least one R of $R_1$, $R_2$ and $R_3$ is substituted or unsubstituted aryl, and the hydroxylamine is selected from:

N-benzylhydroxylamine,
N-(n-nitrobenzyl)hydroxylamine,

-continued

N-(n-methylbenzyl)hydroxylamine,
N-(n-chlorobenzyl)hydroxylamine,
N-(n-aminobenzyl)hydroxylamine,
N-(n-hydroxybenzyl)hydroxylamine,
N-(1,3-diaminobenzyl)hydroxylamine,
N-(1,3-hydroxybenzyl)hydroxylamine,
N-(2,4-diaminobenzyl)hydroxylamine,
N-(2,4-dihydroxybenzyl)hydroxylamine,
Imidazole-2-methylhydroxylamine and
Benzoxazole-2-methylhydroxylamine,
wherein n is selected from 1, 2, 3, 4, 5 and 6.

wherein n is selected from 1, 2, 3, 4, 5 and 6.

9. A composition according to claim 1, wherein at least one R of $R_1$, $R_2$ and $R_3$ is substituted or unsubstituted (C1–C18) oxyl.

10. A composition according to claim 1, wherein at least one R of $R_1$, $R_2$ and $R_3$ is substituted or unsubstituted (C1–C18) oxyl and the R is selected from: hydroxyl, hydroxyalkyl $(O-(CH_2)_{n1})$, hydroxyaryl selected from benzylalcohol, phenol and naphthol, alkoxy $(O-(CH_2)_{n1})$ and aryloxy selected from phenoxy, benzyloxy and naphthyloxy, wherein n1=1 to 18.

11. A composition according to claim 1, wherein at least one R of $R_1$, $R_2$ and $R_3$ is substituted or unsubstituted (C1–C18)alkyl hydroxyl or arylhydroxyl and the hydroxylamine is selected from:

N-(hydroxymethyl)hydroxylamine,
N-(2-hydroxymethyl)hydroxylamine,
N-(3-hydroxypropyl)hydroxylamine,
N-(4-hydroxybutyl)hydroxylamine,
N-(6-hydroxyhexyl)hydroxylamine,
N-(12-hydroxydodecyl)hydroxylamine,
N-(methoxymethyl)hydroxylamine,
N-(methoxyethyl)hydroxylamine,
N-(methoxyisopropyl)hydroxylamine,
N-(benzyloxymethyl)hydroxylamine and
N-(4-hydroxymethylbenzyl)hydroxylamine.

12. A composition according to claim 1, wherein at least one R of $R_1$, $R_2$ and $R_3$ is substituted or unsubstituted (C1–C18) alkylcarboxyl or arylcarboxyl.

13. A composition according to claim 1, wherein at least one R of $R_1$, $R_2$ and $R_3$ is substituted or unsubstituted (C1–C18) alkyl or aryl carboxyl and the R is selected from carboxyalkyls and benzyl.

14. A composition according to claim 1, wherein at least one R of $R_1$, $R_2$ and $R_3$ is substituted or unsubstituted alkyl (C1–C18) or arylcarboxyl and the hydroxylamine is selected from:

N-(carboxymethyl)hydroxylamine,
N-(2-carboxyethyl)hydroxylamine,
N-(3-carboxypropyl)hydroxylamine,
N-(4-carboxybutyl)hydroxylamine,
N-(5-carboxypentyl) hydroxylamine,
N-(6-carboxyhexyl)hydroxylamine,
N-(4-carboxybenzyl)hydroxylamine and
N-(12-carboxydodecyl)hydroxylamine.

15. A composition according to claim 1, wherein at least one R of $R_1$, $R_2$ and $R_3$ is substituted or unsubstituted (C1–C18) ester.

16. A composition according to claim 1, wherein at least one R of $R_1$, $R_2$ and $R_3$ is substituted or unsubstituted (C1–C18) ester and the R is selected from alkyl (C1–C18) and aryl esters.

17. A composition according to claim 1, wherein at least one R of $R_1$, $R_2$ and $R_3$ is substituted or unsubstituted alkyl (C1–C18) or arylesters and the hydroxylamine is selected from:

N-(acetyloxymethyl)hydroxylamine,
N-(acetyloxyethyl)hydroxylamine,
N-(acetyloxypropyl)hydroxylamine,
N-(propylcarbonyloxy)methylhydroxylamine,
N-(butylcarboxyloxy)methylhydroxylamine,
N-(tert-butyloxycarboxyl)methylhydroxylamine,
N-(benzyloxycarbonyl)methylhydroxylamine,
N-(phenyloxycarbonyl)methylhydroxylamine,
N-3-pyridyloxycarbonyl)methylhydroxylamine and
N-(benzoxazol-5-carbonyloxy)methylhydroxylamine.

18. A composition according to claim 1, wherein at least one R of $R_1$, $R_2$ and $R_3$ is substituted or unsubstituted (C1–C18) carbonyl.

19. A composition according to claim 1, wherein at least one R of $R_1$, $R_2$ and $R_3$ is substituted or unsubstituted carbonyl and the R is selected from alkyl (C1 –C18) carbonyls and aryl carbonyls.

20. A composition according to claim 1, wherein at least one R of $R_1$, $R_2$ and $R_3$ is substituted or unsubstituted alkyl (C1–C18) or arylcarbonyls and the hydroxylamine is selected from:

N-(acetyl)methylhydroxylamine,
N-(ethylcarbonyl)methylhydroxylamine,
N-(butylcarbonyl)methylhydroxylamine,
N-(phenylcarbonyl)methylhydroxylamine and
N-(benzylcarbonyl)methylhydroxylamine.

21. A composition according to claim 1, wherein at least one R of $R_1$, $R_2$ and $R_3$ is substituted or unsubstituted alkyl(C1–C18) or aryl amino.

22. A composition according to claim 1, wherein at least one R of $R_1$, $R_2$ and $R_3$ is substituted or unsubstituted alkyl (C1–C18) or aryl amino and the R is selected from primary alkyl amine selected from methylamine, ethylamine, propylamine, butylamine and hexylamine, secondary amine selected from dimethylamine, diethylamine and dipropylamine, tertiary amine selected from trimethyl and trietylamine, and quarternary amine selected from tetramethyl and tetra-ethylammonium salts.

23. A composition according to claim 1, wherein at least one R of $R_1$, $R_2$ and $R_1$ is substituted or unsubstituted alkyl(C1–C18) or aryl amine and the hydroxylamine is selected from:

N-aminomethylhydroxylamine,
N-(2aminoethyl)hydroxlamine,
N-(N-methylamino)methylhydroxylamine,
N-(N,N-dimethylamino)methylhydroxylamine,
N-(N,N,N-trimethylammonium)methylhydroxylamine,
N-(3aminopropyl)hydroxylamine,
N-(6-aminohexyl)hydroxylamine,
N-(4-aminobenzyl)hydroxylamine,
Hydroxylamine -1-methylpyridinium and
Hydroxylamine-1-methylquinolinium.

24. A composition according to claim 1, wherein at least one R of $R_1$, $R_2$ and $R_3$ is substituted or unsubstituted (C1–C8) alkyl or aryl nitro.

25. A composition according to claim 1, wherein at least one R of $R_1$, $R_2$ and $R_3$ is substituted or unsubstituted alkyl(C1–C18) or aryl nitro and the R is selected from alkylnitro selected from nitromethyl, nitroethyl, nitropropyl, nitrobutyl, nitropentyl, nitrohexyl and nitrobenzyl, and arylnitro selected from nitrophenyl and nitronaphthyl.

26. A composition according to claim 1, wherein at least one R of $R_1$, $R_2$ and $R_3$ is substituted or unsubstituted alkyl (C1–C18) or aryl nitro and the hydroxylamine is selected from:

N-(nitromethyl)hydroxylamine,
N-(2-nitroethyl)hydroxylamine,
N-(3-nitropropyl)hydroxylamine,
N-(4-nitrobutyl)hydroxylamine,
N-(5-nitropentyl)hydroxylamine,
N-(6-nitrohexyl)hydroxylamine,
N-(4-nitrobenzyl)hydroxylamine and
N-(2,4-dinitrobenzyl)hydroxylamine.

27. A composition according to claim 1, wherein at least one R of $R_1$, $R_2$ and $R_3$ is substituted or unsubstituted (C1–C18) nitroso.

28. A composition according to claim 1, wherein at least one R of $R_1$, $R_2$ and $R_3$ is substituted or unsubstituted (C1–C18) nitroso and the R is selected from aliphatic nitrosoamines and aromatic nitroso.

29. A composition according to claim 1, wherein at least one R of $R_1$, $R_2$ and $R_3$ is substituted or unsubstituted nitroso (C1–C18) and the hydroxylamine is selected from:

N-(N-methyl-N-nitroso-amino)methylhydroxylamine,
N-(N-methyl-N-nitroso-2-amino)ethylhydroxylamine,
N-(N-methyl-N-nitroso-3-amino)propylhydroxylamine and
N-(p-nitroso)benzylhydroxylamine.

30. A composition according to claim 1, wherein at least one R of $R_1$, $R_2$ and $R_3$ is substituted or unsubstituted oxime.

31. A composition according to claim 1, wherein at least one R of $R_1$, $R_2$ and $R_3$ is substituted or unsubstituted (C1–C18) oxime and the R is selected from: acetaldoxime, propionaldoxime, butanaldoxime and benzaldoxime.

32. A composition according to claim 1, wherein at least one R of $R_1$, $R_2$ and $R_3$ is substituted or unsubstituted oxime (C1–C18) and the hydroxylamine is selected from:

Acetaldoxime-3-hydroxylamine,
Propionaldoxime-4-hydroxylamine,
Butanaldoxime-5-hydroxylamine and
(4-benzaldoxime)1-methylhydroxylamine.

33. A composition according to claim 1, wherein at least one R of $R_1$, $R_2$ and $R_3$ is substituted or unsubstituted (C1–C10) hydrazone.

34. A composition according to claim 1, wherein at least one R of $R_1$, $R_2$ and $R_3$ is substituted or unsubstituted (C1–C10) hydrazone and the R is selected from: acetaldehyde hydrazone, propanaldehyde hydrozone, butanaldehyde hydrazone and phenylhydrazone.

35. A composition according to claim 1, wherein at least one R of $R_1$, $R_2$ and $R_3$ is substituted or unsubstituted hydrazone (C1–C10) and the hydroxylamine is selected from 1-hydroxylamine-acetaldehyde hydrazone,
1-hydroxylamine-propanaldehyde hydrazone,
1-hydroxylamine-butanaldehyde hydrazone and
1-hydroxylamine-benzylaldehyde hydrazone.

36. A composition according to claim 1, wherein at least one R of $R_1$, $R_2$ and $R_3$ is substituted or unsubstituted azo.

37. A composition according to claim 1, wherein at least one R of $R_1$, $R_2$ and $R_3$ is substituted or unsubstituted azo and the R is selected from: azobenzene, p-(phenylazo)benzyl and p-diazobenzyl.

38. A composition according to claim 1, wherein at least one R of $R_1$, $R_2$ and $R_3$ is substituted or unsubstituted azo and the hydroxylamine is selected from:

N-(p-phenylazo)benzylhydroxylamine,

N-(p-diazobenzyl)hydroxylamine and

N-(p-methoxylphenylazo)benzylhydroxylamine.

39. A composition according to claim 1, wherein at least one R of $R_1$, $R_2$ and $R_3$ is substituted or unsubstituted (C1–C18) thiol.

40. A composition according to claim 1, wherein at least one R of $R_1$, $R_2$ and $R_3$ is substituted or unsubstituted (C1–C18) thiol and the R is selected from (C1–C18) alkylthiol selected from methyl, ethyl, propyl, butyl, pentyl and hexyl thiol, and arylthiol selected from thiophenol and benzylthiol.

41. A composition according to claim 1, wherein at least one R of $R_1$, $R_2$ and $R_3$ is substituted or unsubstituted (C1–C18) thiol and the hydroxylamine is selected from:

N-(thiomethyl)hydroxylamine,
N-(2-thioethyl)hydroxylamine,
N-(3-thiopropyl)hydroxylamine and
N-(p-sulfhydryl)benzylhydroxylamine 42. A composition according to claim 1, wherein at least one R of $R_1$, $R_2$ and $R_3$ is substituted or unsubstituted (C1–C18) sulfonic acid.

43. A composition according to claim 1, wherein at least one R of $R_1$, $R_2$ and $R_3$ is substituted or unsubstituted (C1–C18) sulfonic acid and the R is selected from methanesulfonic acid, ethanesulfonic acid, propanesulfonic acid, butanesulfonic acid and p-toluenesulfonic acid.

44. A composition according to claim 1, wherein at least one R of $R_1$, $R_2$ and $R_3$ is substituted or unsubstituted (C1–C18) sulfonic acid and the hydroxylamine is selected from:

1-hydroxylamine-methanesulfonic acid,
1-hydroxylamine-ethane-2-sulfonic acid,
1-hydroxylamine-propane-3-sulfonic acid,
1-hydroxylamine-butane-4-sulfonic acid and
N-(p-sulfobenzyl)hydroxylamine.

45. A composition according to claim 1, wherein at least one R of $R_1$, $R_2$ and $R_3$ is halide.

46. A composition according to claim 1, wherein at least one R of $R_1$, $R_2$ and $R_3$ is halide and the R is selected from F, Cl, Br and I.

47. A composition according to claim 1, wherein at least one R of $R_1$, $R_2$ and $R_3$ is halide and the hydroxylamine is selected from:

N-(chloromethyl)hydroxylamine,
N-(bromomethyl)hydroxylamine,
N-(2-chloroethyl)hydroxylamine,
N-(3-chloropropyl)hydroxylamine,
N-(4-chlorobutyl)hydroxylamine,
N-(p-chlorobenzyl)hydroxylamine,
N-(p-fluorobenzyl)hydroxylamine and
N-(p-iodobenzyl)hydroxylamine.

48. A composition according to claim 1, wherein at least one R of $R_1$, $R_2$ and $R_3$ is substituted or unsubstituted hydroxylamine.

49. A composition according to claim 1, wherein at least one R of $R_1$, $R_2$ and $R_3$ is substituted or unsubstituted hydroxylamine and R is selected from N-methylhydroxylamine, N-ethylhydroxylamine, N-propylhydroxylamine N-butylhydroxylamine, N-pentylhydroxylamine, and N-benzylhydroxylamine.

50. A composition according to claim 1, wherein at least one R of $R_1$, $R_2$ and $R_3$ is substituted or unsubstituted hydroxylamine and the hydroxylamine is selected from:

Bis-methylhydroxylamine,
Bis-(2-ethyl)hydroxylamine,
Bis-(3-propyl)hydroxylamine and
Bis-benzylhdyroxylamine.

51. A composition according to claim 1, wherein at least one R of $R_1$, $R_2$ and $R_3$ is substituted or unsubstituted (C1–C18) phosphoester.

52. A composition according to claim 1 wherein at least one R of $R_1$, $R_2$ and $R_3$ is substituted or unsubstituted (C1–C18) phosphoester and the R is selected from: dimethylphosphate, diethylphosphate, dipropylphosphate and benzylphosphate.

53. A composition according to claim 1, wherein at least one R of $R_1$, $R_2$ and $R_3$ is substituted or unsubstituted (C1–C18) phosphoester and the hydroxylamine is selected from:

di-hydroxylaminemethylphosphate ester, mono-hydroxylaminemethylphosphate ester, mono-(1-hydroxylamine)-ethyl-2-phosphate ester, di-(1-hydroxylamine)-2-ethylphosphate ester, di-(1-hydroxylamine)-3-propyl-phosphate ester, mono-(hydroxylamine-benzyl-phosphate ester and di-hydroxylamine-benzylphosphateester.

54. A composition according to claim 1, wherein the nitrone is less than 1% (wt/wt) of the hydroxylamine in the composition.

55. A composition according to claim 1 further comprising an effective amount of a carnitine.

56. A method for reducing oxidative damage to, or delaying senescence of a cell comprising the step of contacting a cell subject to or at risk of undesirable oxidative damage or senescence with a composition according to claim 1.

57. A method for reducing oxidative damage to, or delaying senescence of a cell comprising the steps of:

identifying a cell as subject to or at risk of undesirable oxidative damage or senescence; and contacting the cell with a composition according to claim 1.

58. A method according to claim 57, wherein the cell is contained in other than a cancerous host.

* * * * *

UNITED STATES PATENT AND TRADEMARK OFFICE
CERTIFICATE OF CORRECTION

PATENT NO. : 6,455,589 B1
DATED : September 24, 2002
INVENTOR(S) : Ames et al.

It is certified that error appears in the above-identified patent and that said Letters Patent is hereby corrected as shown below:

Column 37,
Line 10, "N-hydroxyl amine" should be -- N-hydroxylamine --.

Column 38,
Line 21, after "hydroxyalkyl", "(O-$(CH_2)_{n1}$)" should be -- (HO-$(CH_2)_{n1}$) --.
Line 32, "N-(2-hydroxymethyl)hydroxylamine" should be
-- N-(2-hydroxyethyl)hydroxylamine --.

Column 39,
Line 53, "N-(2aminoethyl)hydroxlamine" should be
-- N-(2-aminoethyl)hydroxlamine --.
Line 57, "N-(3aminopropyl)hydroxylamine" should be
-- N-(3-aminopropyl)hydroxylamine --.

Signed and Sealed this

Seventeenth Day of December, 2002

JAMES E. ROGAN
*Director of the United States Patent and Trademark Office*